(12) United States Patent
Hu et al.

(10) Patent No.: US 11,908,580 B2
(45) Date of Patent: Feb. 20, 2024

(54) IMAGE CLASSIFICATION METHOD, COMPUTER-READABLE STORAGE MEDIUM, AND COMPUTER DEVICE

(71) Applicant: Tencent Technology (Shenzhen) Company Limited, Shenzhen (CN)

(72) Inventors: Yifan Hu, Shenzhen (CN); Yefeng Zheng, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 284 days.

(21) Appl. No.: 17/397,857

(22) Filed: Aug. 9, 2021

(65) Prior Publication Data

US 2021/0365741 A1 Nov. 25, 2021

Related U.S. Application Data

(63) Continuation of application No. PCT/CN2020/085062, filed on Apr. 16, 2020.

(30) Foreign Application Priority Data

May 8, 2019 (CN) .......................... 201910379277.2

(51) Int. Cl.
*G16H 50/20* (2018.01)
*G16H 30/40* (2018.01)
(Continued)

(52) U.S. Cl.
CPC .......... *G16H 50/20* (2018.01); *G06F 18/214* (2023.01); *G06F 18/217* (2023.01); *G06F 18/22* (2023.01);
(Continued)

(58) Field of Classification Search
CPC ................. G06V 10/25; G06V 10/467; G06T 2207/30096
See application file for complete search history.

(56) References Cited

U.S. PATENT DOCUMENTS 9,092,691 B1 * 7/2015 Beaumont .............. G06V 10/25

FOREIGN PATENT DOCUMENTS

| CN | 101669828 A | 3/2010 |
| CN | 107633522 * | 1/2018 |

(Continued)

OTHER PUBLICATIONS

Li et al., "A Deep Dual-Path Network for Improved Mammogram Image Processing", School of Engineering, University of Edinburgh, Edinburgh, United Kingdom, Mar. 1, 2019, 5 pgs.

(Continued)

*Primary Examiner* — Ross Varndell
(74) *Attorney, Agent, or Firm* — Morgan, Lewis & Bockius LLP

(57) ABSTRACT

A computer device obtains a plurality of medical images. The device generates a texture image based on image data of a region of interest in the medical images. The device extracts a local feature from the texture image using a first network model. The device extracts a global feature from the medical images using a second network model. The device fuses the extracted local feature and the extracted global feature to form a fused feature. The device performs image classification based on the fused feature.

19 Claims, 10 Drawing Sheets

(51) Int. Cl.
*G06V 10/25* (2022.01)
*G06V 10/26* (2022.01)
*G06F 18/21* (2023.01)
*G06F 18/22* (2023.01)
*G06F 18/214* (2023.01)
*G06F 18/25* (2023.01)
*G06F 18/2413* (2023.01)
*G06V 10/764* (2022.01)
*G06V 10/774* (2022.01)
*G06V 10/776* (2022.01)
*G06V 10/80* (2022.01)
*G06V 10/44* (2022.01)
*G06N 3/08* (2023.01)

(52) U.S. Cl.
CPC ........ *G06F 18/2413* (2023.01); *G06F 18/253* (2023.01); *G06V 10/25* (2022.01); *G06V 10/26* (2022.01); *G06V 10/454* (2022.01); *G06V 10/764* (2022.01); *G06V 10/774* (2022.01); *G06V 10/776* (2022.01); *G06V 10/806* (2022.01); *G16H 30/40* (2018.01); *G06N 3/08* (2013.01); *G06V 2201/03* (2022.01)

(56) References Cited

FOREIGN PATENT DOCUMENTS

| CN | 107862340 A | 3/2018 |
| CN | 107945179 A | 4/2018 |
| CN | 108364006 A | 8/2018 |
| CN | 108428229 A | 8/2018 |
| CN | 108491835 A | 9/2018 |
| CN | 109034269 A | 12/2018 |
| CN | 109035197 A | 12/2018 |
| CN | 109117879 A | 1/2019 |
| CN | 109284749 A | 1/2019 |
| CN | 110321920 A | 10/2019 |

OTHER PUBLICATIONS

Tencent Technology, ISR, PCT/CN2020/085062, dated Jul. 20, 2020, 2 pgs.
Tencent Technology, WO, PCT/CN2020/085062, dated Jul. 20, 2020, 5 pgs.
Tencent Technology, IPRP, PCT/CN2020/085062, dated Nov. 2, 2021, 6 pgs.

* cited by examiner

IMAGE CLASSIFICATION METHOD, COMPUTER-READABLE STORAGE MEDIUM, AND COMPUTER DEVICE

CROSS-REFERENCE TO RELATED APPLICATIONS

This application is a continuation application of PCT Patent Application No. PCT/CN2020/085062, entitled "IMAGE CLASSIFICATION METHOD, COMPUTER READABLE STORAGE MEDIUM, AND COMPUTER DEVICE" filed on Apr. 16, 2020, which claims priority to Chinese Patent Application No. 201910379277.2, filed with the State Intellectual Property Office of the People's Republic of China on May 8, 2019, and entitled "IMAGE CLASSIFICATION METHOD AND APPARATUS, COMPUTER-READABLE STORAGE MEDIUM, AND COMPUTER DEVICE", all of which are incorporated herein by reference in their entirety.

FIELD OF THE TECHNOLOGY

This application relates to the field of image processing technologies, and in particular, to an image classification method, a computer-readable storage medium, and a computer device.

BACKGROUND OF THE DISCLOSURE

With constant development of image processing technologies, the image processing technologies are widely applied to the medical field. For example, medical images of a human body or a part of a human body are classified, and whether a corresponding lesion appears may be determined based on a medical image classification result.

In a conventional medical image classification solution, a neural network-based classification model is mainly used, to be specific, medical images are inputted to the neural network-based classification model for classification. However, when there are a large quantity of complex features in the medical images, the accuracy of a medical image classification result is like to be low.

SUMMARY

Embodiments of this application provide an image classification method and apparatus, a computer-readable storage medium, and a computer device, to resolve a technical problem of low accuracy of a medical image classification result.

In accordance with some embodiments, an image classification method is provided, applicable to a computer device, including:
  obtaining medical images that are to be classified;
  generating a texture image based on image data of a region of interest (ROI) in the medical images;
  extracting a local feature (e.g., a local medical feature) from the texture image using a first network model;
  extracting a global feature (e.g., a global medical feature) from the medical images using a second network model;
  fusing the extracted local feature and the extracted global feature to form a fused feature, and performing image classification based on the fused feature.

In accordance with some embodiments, an image classification apparatus is provided, including:
  an image obtaining module, configured to obtain medical images that are to be classified;
  an image generation module, configured to generate a texture image based on image data of a region of interest in the medical images;
  a first feature extraction module, configured to perform feature extraction on the texture image by using a first network model, to obtain a local medical feature;
  a second feature extraction module, configured to perform feature extraction on the medical images by using a second network model, to obtain a global medical feature; and
  an image classification module, configured to perform image classification based on a fused feature of the global medical feature and the local medical feature.

In accordance with some embodiments, a non-transitory computer-readable storage medium is provided, storing a computer program, the computer program, when executed by one or more processors, causing the processors to perform any of the methods disclosed herein.

In accordance with some embodiments, a computer device is provided, the computer device including memory and one or more processors, the memory storing a computer program, the computer program, when executed by the processors, cause the processors to perform any of the methods disclosed herein.

DESCRIPTION OF EMBODIMENTS

To make the objectives, technical solutions, and advantages of this application clearer and more understandable, this application is further described in detail below with reference to the accompanying drawings and the embodiments. It is to be understood that the specific embodiments described herein are only used for describing this application, but are not intended to limit this application.

Figure 1:
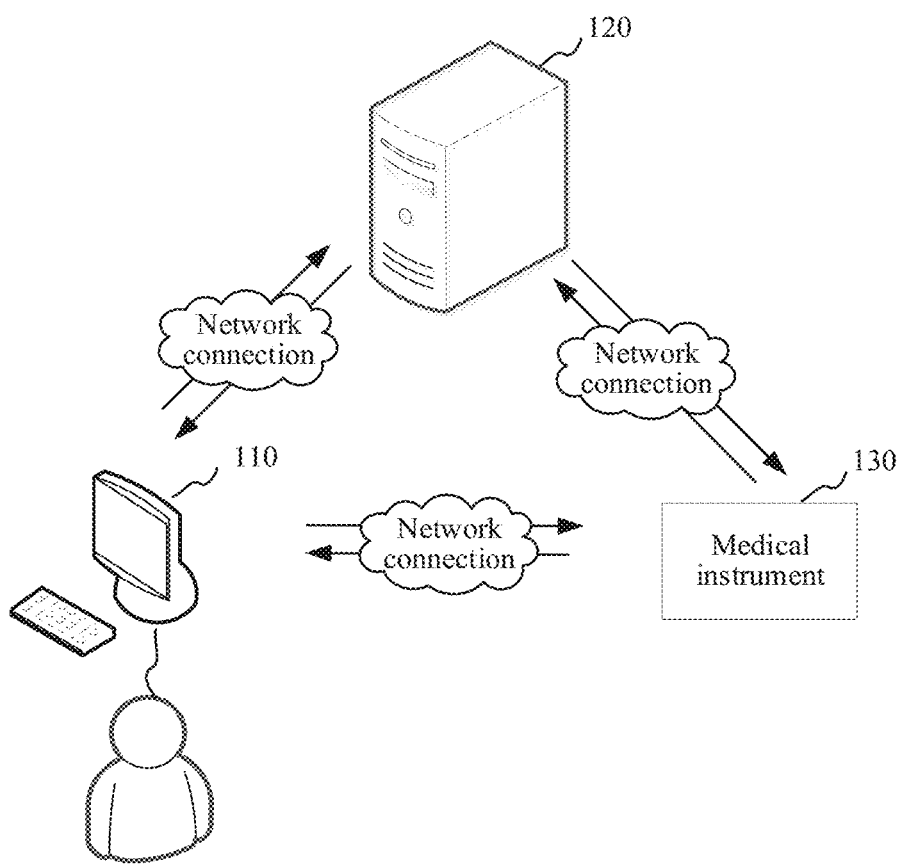
FIG. 1 is a diagram of an application environment of an image classification method according to an embodiment.

FIG. 1 is a diagram of an application environment of an image classification method according to an embodiment. Referring to FIG. 1, the image classification method is applicable to an image classification system. The image classification system includes a terminal 110, a server 120, and a medical instrument 130. The terminal 110, the server 120, and the medical instrument 130 are connected via a network. The network may be a wire network or may be a wireless network. The terminal 110 may be a device on which an end-to-end automatic classification and diagnosis system is installed, and may be specifically a desktop terminal or a mobile terminal. The mobile terminal may be specifically at least one of a mobile phone, a tablet computer, a notebook computer, or the like. The server 120 may be implemented by an independent server or a server cluster that includes a plurality of servers. The medical instrument 130 may be a computed tomography (CT) machine, a magnetic resonance imaging (MRI) device, an ultrasound diagnostic instrument, an X-ray machine, an electrocardiogram device, an electroencephalogram device, or the like.

Figure 2:
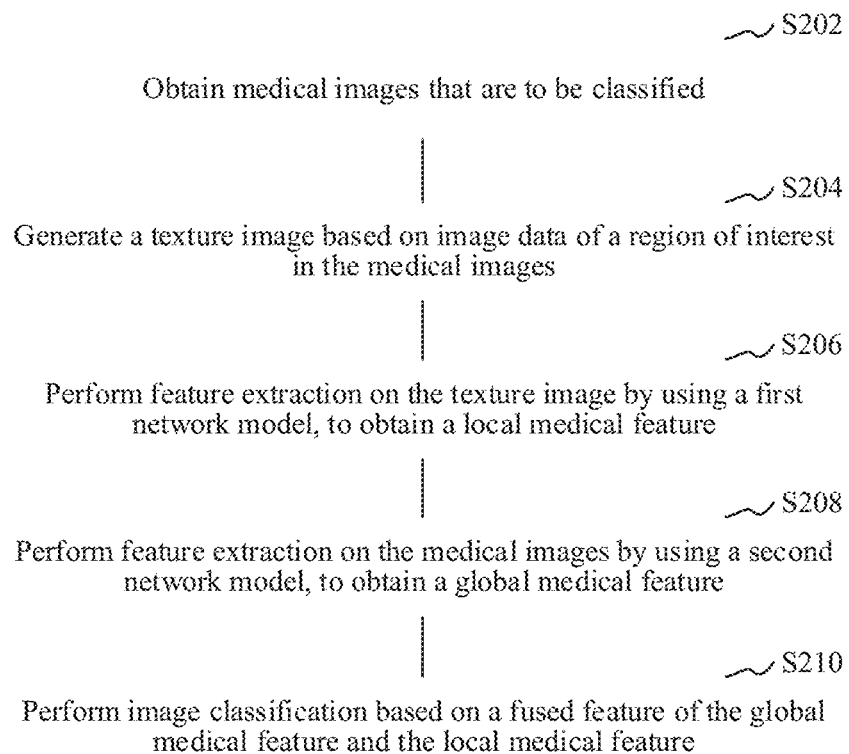
FIG. 2 is a schematic flowchart of an image classification method according to an embodiment.

As shown in FIG. 2, in an embodiment, an image classification method is provided. The method may be applicable to the terminal 110 or the server 120 in FIG. 1. In this embodiment, the method being applied to the terminal 110 in FIG. 1 is used as an example for description mainly. Referring to FIG. 2, the image classification method specifically includes the following steps:

S202. Obtain medical images that are to be classified.

The medical images may be images of different data domains, e.g., images of different modalities formed by scanning a human body or a part of a human body by using different medical instruments. Medical images obtained in different medical application scenarios belong to different data domains. The data domain may represent that a medical image belongs to a medical device or an imaging modality.

For example, the medical image may be a CT image obtained by a CT machine, an MRI image obtained by an MRI device, or an ultrasound image obtained by an ultrasound diagnostic instrument. In addition, the medical image may alternatively be an X-ray image, an electrocardiogram, an electroencephalogram, or the like. In the medical field, inherent heterogeneity of different symptoms may be reflected in medical images. For example, appearances (such as shapes and sizes) of a part of human bodies have different degrees of differences. Therefore, medical images can be used as a medical judgment method or reference factor to assist clinical diagnosis.

In an embodiment, a terminal selects an instruction based on an inputted image, to select a corresponding medical image from an image database; or a terminal establishes a communication connection such as a wired communication connection or a wireless communication connection to a medical instrument, and obtains, when the medical instrument generates a medical image through scanning, the medical image generated by the medical instrument.

In an embodiment, after obtaining a medical image that is to be classified, the terminal may further perform artifact recognition on the obtained medical image to determine whether there is an artifact in the medical image and a severity value of the artifact. Alternatively, after obtaining a medical image that is to be classified, the terminal outputs the medical image for presentation; and when receiving an artifact confirmation instruction for the medical image, determines that the medical image includes an artifact and a severity value corresponding to the included artifact. If the medical image includes an artifact and a severity value of the artifact is relatively large, the terminal may obtain a medical image again. If the medical image includes an artifact but a severity value of the artifact is relatively small, or the medical image includes no artifact, S204 is performed.

Artifacts may mean that some images that do not exist in the human body but can degrade image quality appear during magnetic resonance scanning or information processing of the terminal. For example, a main reason for appearance of a motion artifact is that during the magnetic resonance scanning of the terminal, a position or a shape of a moving organ during each excitation, encoding, and signal collection has changed. Therefore, the artifact is caused due to a phase error.

In another embodiment, when an obtained medical image has an artifact and a severity value of the artifact is greater than a target threshold, the terminal may further increase a sampling time to reduce a bandwidth, so as to reduce ripples. In addition, the terminal may further reduce a pixel size by increasing a phase encoding number to reduce discontinuity between pixels, so as to reduce tail wave oscillations.

S204. Generate a texture image based on image data in a region of interest in the medical images.

The region of interest (ROI) may be a region having a particular feature that is a point of interest. The region may be marked by a professional (for example, a doctor), or may be obtained by segmenting the medical images by using a machine learning model or another image segmentation algorithm. In an actual medical application scenario, the ROI is usually a region in which a part of a human body has a lesion (that is, a lesion region).

In an embodiment, when no ROI is defined in obtained medical images, the terminal may divide the medical images according to an inputted instruction to obtain the ROI, or the terminal may obtain the ROI by learning the ROI by using a machine learning model. In addition, the medical images obtained by the terminal may include a defined ROI.

For the ROI, region segmentation may be performed on the medical images in the following three manners:

Manner 1: The ROI is obtained by segmentation through supervised learning.

In an embodiment, a manner of obtaining the ROI includes: The terminal obtains medical image samples having segmentation labels; inputs the medical image samples to an image segmentation network for segmentation, so that a parameter value of the image segmentation network is updated iteratively to obtain a predicted ROI; and inputs the obtained medical images to a trained image segmentation network for image segmentation when the predicted ROI matches the segmentation labels, to obtain the ROI of the medical images.

The medical image samples may also be images of different data domains, that is, images of different modalities formed by scanning a human body or a part of a human body by using different medical instruments.

In an embodiment, the step of inputting the obtained medical images to a trained image segmentation network for image segmentation to obtain the ROI of the medical images may include: The terminal inputs the obtained medical images to the trained image segmentation network; performs feature extraction on the medical images by using the image segmentation network, to obtain an image feature of a target object in the medical images; and inputs the obtained image feature to the image segmentation network for processing, to obtain the ROI of the medical images.

For example, the terminal obtains medical image samples having segmentation labels, then trains an image segmentation network by using the medical image samples having the segmentation labels, and obtains a trained image segmentation network when an output of the image segmentation network gradually becomes stable (in other words, when an obtained ROI is consistent with the segmentation labels). Then, the terminal inputs the obtained medical images to the trained image segmentation network for image segmentation, to obtain the ROI of the medical images.

In another example, when a quantity of the obtained medical images is relatively large, some of the medical images may be marked to obtain medical image samples having segmentation labels. Then, an image segmentation network is trained by using the medical image samples having the segmentation labels, and a trained image segmentation network is obtained when an output of the image segmentation network gradually becomes stable (in other words, when an obtained ROI is consistent with the segmentation labels). The terminal inputs the obtained medical images that are not marked to the trained image segmentation network for image segmentation, to obtain the ROI of the medical images.

Manner 2: The ROI is obtained by segmentation through unsupervised learning.

In an embodiment, a manner of obtaining the ROI includes: The terminal obtains pixel values of medical images, and obtains, when the pixel values meet a target condition, a region corresponding to the pixel values meeting the target condition as the ROI.

The ROI may be a pathological region. There is heterogeneity between a pathological portion and a healthy portion. Therefore, a pixel value of the pathological portion is different from a pixel value of the healthy portion. A target condition may be set. When a pixel value meets the target condition, a region in which the pixel value is located is obtained as the ROI.

The target condition may be a pixel threshold. If the pixel value of the pathological region is greater than the pixel value of the healthy region, whether the pixel value is greater than the pixel threshold is determined. If the pixel value is greater than the pixel threshold, a region in which the pixel value greater than the pixel threshold is located is obtained as the ROI. If the pixel value of the pathological region is less than the pixel value of the healthy region, whether the pixel value is less than the pixel threshold is determined. If the pixel value is less than the pixel threshold, a region in which the pixel value less than the pixel threshold is located is obtained as the ROI. The pixel threshold may be set flexibly based on actual medical applications.

Manner 3: The ROI is obtained by segmentation manually.

In an embodiment, a manner of obtaining the ROI includes: The terminal obtains an inputted ROI definition instruction, and defines an ROI corresponding to the ROI definition instruction in medical images.

For example, when a quantity of medical images is relatively small, the ROI may be defined through manual marking. When receiving an ROI definition instruction (for example, drawing on medical images displayed on the terminal) issued by a doctor or other technical personnel, the terminal draws an ROI corresponding to the ROI definition instruction in the medical images.

In an embodiment, the terminal extracts a texture feature matrix from the ROI of the medical images. The texture feature matrix may be any one of a gray-level co-occurrence matrix (GLCM), a gray-level run-length matrix (GLRLM), a gray level size zone matrix (GLSZM), or a gray scale gradient matrix (GSGM).

In an embodiment, the step of extracting a texture feature matrix from the ROI of the medical images may specifically include: The terminal first unifies pixel value intervals of the medical images, and then calculates a frequency at which a target pixel combination appears in the ROI of the medical images and in a target calculation direction, to obtain the texture feature matrix. The pixel value interval may be [0, N].

Figure 3:
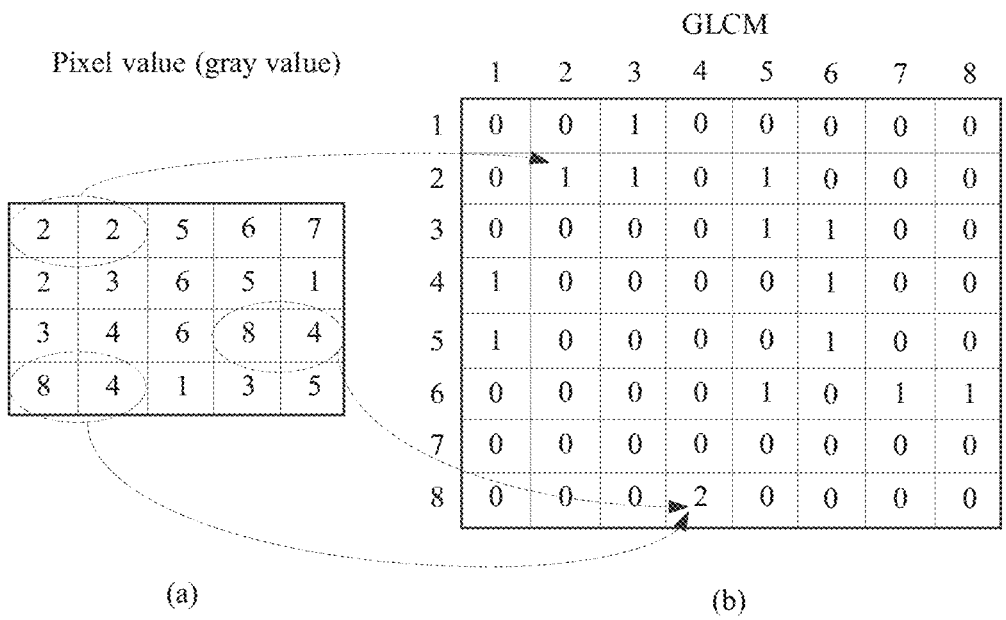
FIG. 3 is a schematic diagram of obtaining a texture feature matrix according to an embodiment.

For example, as shown in FIG. 3, (a) in FIG. 3 shows pixel values in an ROI. A pixel combination GLCM(1, 1) represents a frequency (that is, a number of times) at which pixel values 1 appear in the ROI and in a 0° direction at the same time. The terminal determines a count (e.g., calculates the frequency) at which GLCM(1, 1) appears in the ROI and in the 0° direction at the same time. As can be seen from the figure, the frequency at which GLCM(1, 1) appears in the ROI and in the 0° direction at the same time is 0. In this case, 0 is recorded at a corresponding position in (b) in FIG. 3. Similarly, a frequency at which GLCM(8, 4) appears in the ROI and in the 0° direction at the same time is 2. In this case, 2 is recorded at a corresponding position in (b) in FIG. 3. A matrix in (b) in FIG. 3 is obtained after frequencies at which all possible pixel combinations appear in the ROI and in the 0° direction at the same time are calculated. In addition, frequencies at which all the possible pixel combinations appear in the ROI and in 45°, 90°, and 145° directions at the same time are respectively calculated by using the method described above to obtain other three matrices. A mean of frequencies at corresponding positions in the obtained four matrices is calculated to obtain a mean matrix. Frequencies in the mean matrix are converted into probabilities to obtain a probability matrix. The probability matrix is the texture feature matrix. Alternatively, frequencies in the obtained four matrices are respectively converted into probabilities to obtain four probability matrices. A mean of probabilities at corresponding positions in the four probability matrices is calculated to obtain a mean matrix. The mean matrix is the texture feature matrix.

A manner of respectively converting frequencies in a matrix into probabilities may be: dividing a frequency in the matrix by total frequencies in the matrix to obtain a corresponding probability. Calculating the mean of the probabilities at the corresponding positions in the probability matrices may be first summing probabilities corresponding to (1,1) in the four probability matrices, and then calculating a mean to obtain a mean probability.

S206. Perform feature extraction on the texture image by using a first network model, to obtain a local medical feature.

The first network model may be a network branch in a deep learning network model. The deep learning network model may be a deep convolutional neural network (DCNN) model. As a network branch in the deep learning network model, the first network model may belong to the VGG network, the Inception network, the ResNet network, the DenseNet network, or the like; or may be formed by a plurality of network layers (for example, a convolutional layer and a pooling layer) of the foregoing networks, the layers being configured to extract the local medical feature. Because the texture image is generated by the image data in the ROI in the medical images, a feature extracted based on the texture image may be referred to as the local medical feature.

The first network model may include a plurality of convolutional layers and at least one pooling layer. In an embodiment, the terminal performs convolution processing on the texture image by using the convolutional layers in the first network model, for example, performs convolution processing on an inputted texture image by using a first convolutional layer, and performs convolution processing on an output result of the first convolutional layer as an input by using a second convolutional layer, and the rest may be deducted by analogy. After performing convolution processing by using the convolutional layers in the first network model, the terminal performs pooling processing on a result obtained after the convolution processing. A result obtained after the pooling processing is the local medical feature.

For example, as shown in Table 1, convolution processing is performed on a texture image by using convolutional layers in Table 1. Then, pooling processing is performed, by using a pooling layer, on a final result obtained after the convolution processing, to obtain a local medical feature.

TABLE 1

Structure table of 2D ResNet for processing a texture image

| Network layer name | Size of an output feature | Network layer |
|---|---|---|
| Conv1 | 48*48 | Convolution kernel size 7 × 7, 8 channels, stride 2 |
| Conv2_x | 24*24 | Maximum pooling of a convolution kernel 3 × 3, stride 2 |
|  |  | Residual network module $\begin{bmatrix} 3\times 3, 8 \\ 3\times 3, 8 \end{bmatrix} \times 2$ |
| Conv3_x | 12*12 | Residual network module $\begin{bmatrix} 3\times 3, 16 \\ 3\times 3, 16 \end{bmatrix} \times 2$ |
| Conv4_x | 6*6 | Residual network module $\begin{bmatrix} 3\times 3, 32 \\ 3\times 3, 32 \end{bmatrix} \times 2$ |
| Average pooling (Avg pool) | 1*1 | Avg pool |

S208. Perform feature extraction on the medical images by using a second network model, to obtain a global medical feature.

The second network model may be another network branch in the deep learning network model, in other words, the deep learning network model includes the first network model and further includes the second network model. The second network model may also belong to the VGG network, the Inception network, the ResNet network, the DenseNet network, or the like; or may be formed by a plurality of network layers (for example, a convolutional layer and a pooling layer) in the foregoing networks, the layers being configured to extract the global medical feature, that is, extract another medical feature outside the ROI in the medical images in addition to a medical feature in the ROI. In addition, the deep learning network model further includes a fully connected layer configured to fuse features extracted by the first network model and the second network model, so as to perform image classification by using a fused feature.

The second network model may include convolutional layers and a pooling layer. In an embodiment, the terminal performs convolution processing on the medical images by using the convolutional layers in the second network model, for example, performs convolution processing on inputted medical images by using a first convolutional layer, and performs convolution processing on an output result of the first convolutional layer as an input by using a second convolutional layer, and the rest may be deducted by analogy, to obtain a final convolution. After performing convolution processing by using the convolutional layers in the second network model, the terminal performs pooling processing on a result obtained after the convolution processing. A result obtained after the pooling processing is the global medical feature.

S210. Perform image classification based on a fused feature of the global medical feature and the local medical feature.

In an embodiment, the terminal fuses the global medical feature and the local medical feature by using the fully connected layer in the deep learning network model, to obtain a fused feature; and then, performs image classification on the medical images based on the fused feature.

In an embodiment, S210 may specifically include: The terminal fuses the global medical feature and the local medical feature by using the fully connected layer, to obtain the fused feature; performs convolution calculation on the fused feature; and performs image classification on the medical images based on a result obtained after the convolution calculation.

For example, as shown in Table 2, if a feature size of the global medical feature is 1024 and a feature size of the local medical feature is 32, the global medical feature and the local medical feature are fused by using the fully connected layer, to obtain a fused feature having a feature size of 1024+32. Then, convolution processing is performed on the fused feature by using the fully connected layer, to obtain a vector with four elements. The elements in the vector are used for representing probabilities (or proportions) that a medical image belongs to corresponding types. Then, a type corresponding to the largest probability is used as a target type of the medical image. The target type may be represented by a number. For example, 0 represents a type A, 1 represents a type B, 2 represents a type C, and 3 represents a type D.

TABLE 2

Fully connected layer of an entire network

| Network layer name | Size of an input feature | Size of an output feature |
|---|---|---|
| Fully connected layer | 1024 + 32 | 4 (a number for representing belonging to a corresponding image type) |

A difference between the first network model and ResNet18 is that one ResNet block is reduced in the first network model, and a quantity of output channels after each convolutional layer is also reduced. Because only 32 features are extracted by using the first network model, only a relatively narrow and shallow network is required to complete the extraction, thereby improving the classification accuracy. Medical features of two branches are fused at the fully connected layer, and there are 1024+32 medical features in total. A final output is a quantity of categories.

Figure 4:
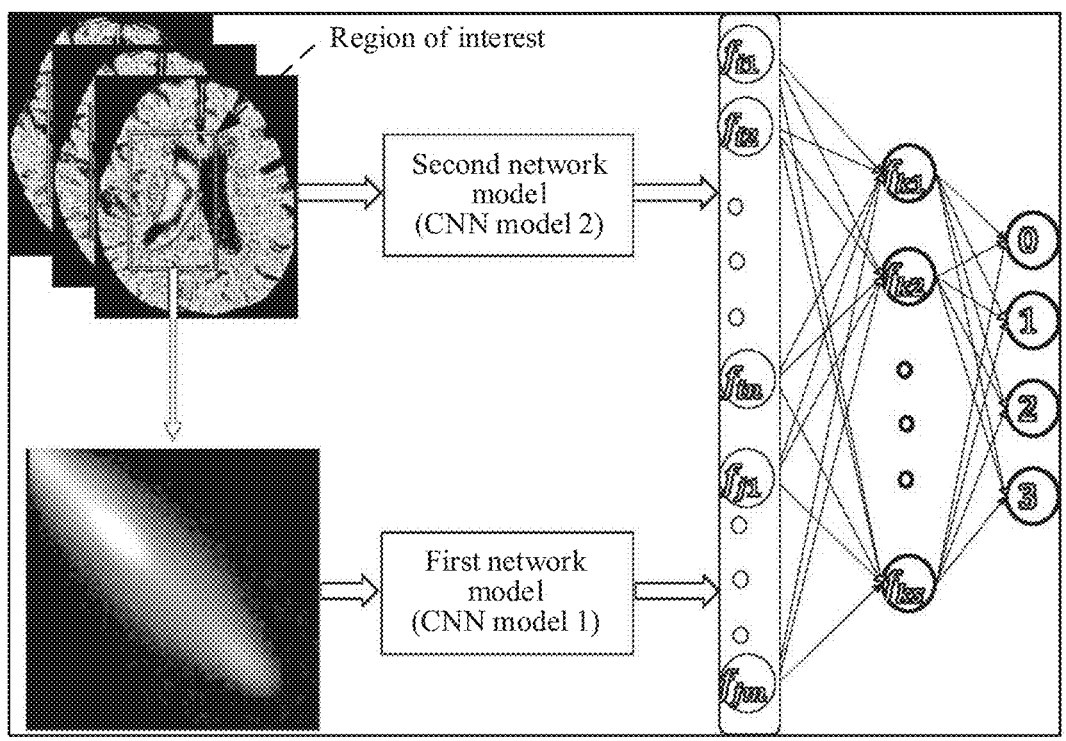
FIG. 4 is a schematic diagram of inputting medical images and a texture image to network models for image classification according to an embodiment.

In an example, as shown in FIG. 4, after medical images are obtained, a texture feature matrix (for example, a GLCM) is extracted from an ROI in the medical images, and the texture feature matrix is mapped to an image of a same size to obtain a texture image. The texture image is inputted to a first network model (that is, a convolutional neural network (CNN) model 1) of a deep learning network model for feature extraction, to obtain a local medical feature $f_{j1}, f_{j2}, \ldots, f_{jm}$. The medical images are inputted to a second network model (that is, a CNN model 2) of the deep learning network model for feature extraction, to obtain a global medical feature $f_{i1}, f_{i2}, \ldots, f_{in}$. The local medical feature $f_{j1}, f_{j2}, \ldots, f_{jm}$ and the global medical feature $f_{i1}, f_{i2}, \ldots, f_{in}$ are fused by using a fully connected layer, to obtain a fused feature $f_{i1}, f_{i2}, \ldots f_{in}, f_{j1}, f_{j2}, \ldots, f_{jm}$. Then, the fused feature is processed to obtain a classification result.

Figure 5:
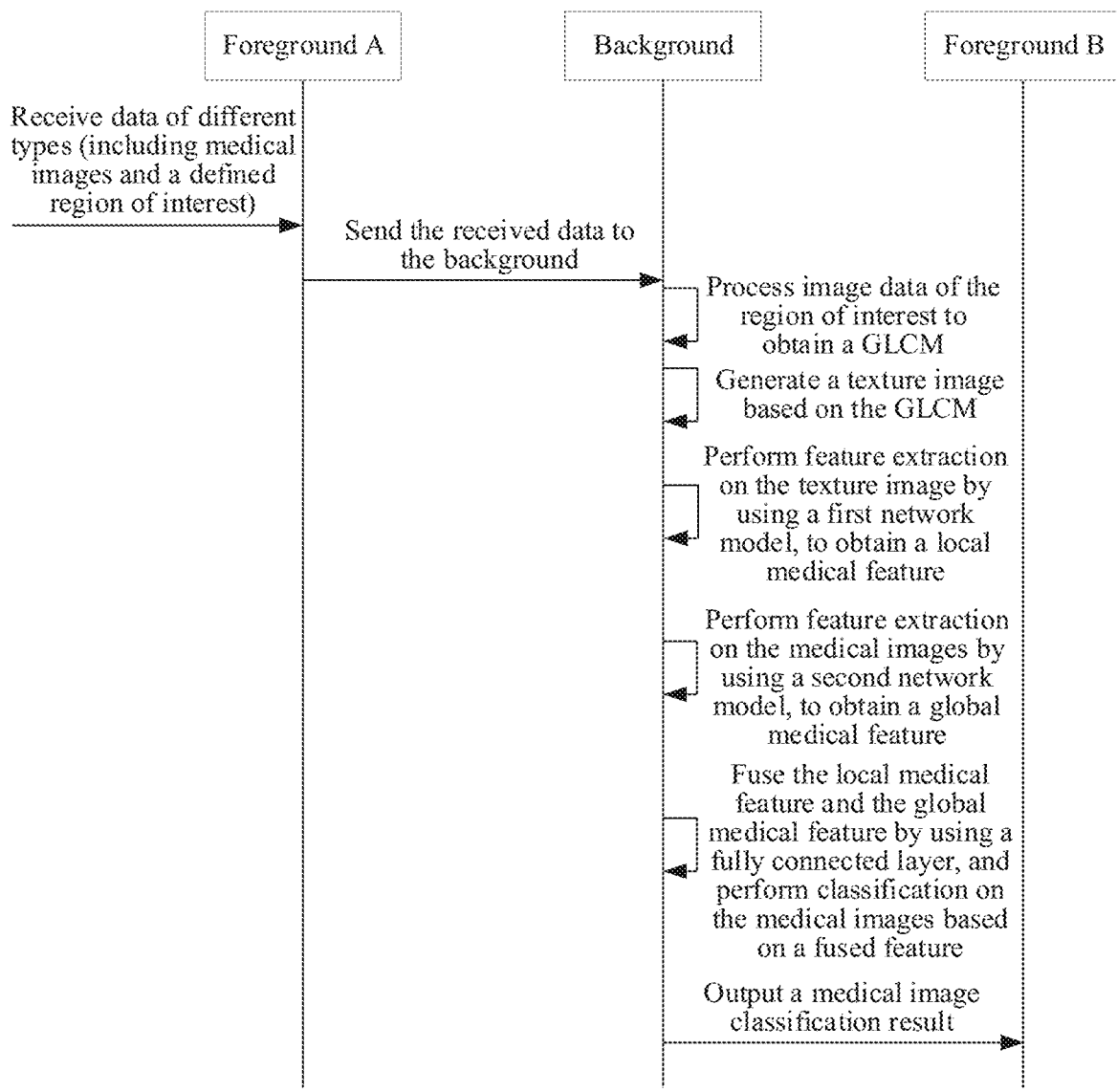
FIG. 5 is a schematic diagram of an image classification method according to an embodiment.

In another example, as shown in FIG. 5, a foreground A obtains different types of medical data (where the medical data may be medical images in which no ROI has been defined or medical images in which an ROI has been defined). Then, the received medical data is sent to a background. When the received medical data is medical images in which an ROI has been defined, the background directly processes image data of the ROI to obtain a GLCM, and generates a texture image based on the GLCM. If the received medical data is medical images in which no ROI has been defined, the background obtains the ROI of the medical images based on a segmentation algorithm, processes image data of the ROI to obtain a GLCM, and generates a texture image based on the GLCM. Then, the background performs feature extraction on the texture image by using a first network model in a deep learning network model, to obtain a local medical feature; performs feature extraction on the medical images by using a second network model in the deep learning network model, to obtain a global medical feature; fuses the local medical feature and the global medical feature at a fully connected layer; classifies the medical images by using a fused feature, to finally obtain a classification result for the medical images; and outputs the classification result to a foreground B. The foreground A may be a medical device configured to obtain a medical image. The background may be a computer device (for example, the foregoing terminal) or a backend server configured to perform feature extraction on a medical image and a texture image, and perform image classification based on an extracted medical feature. The foreground B may be a display device configured to display a medical image classification result.

In the foregoing embodiments, a texture image is generated by using image data of an ROI in medical images. Then, a local feature of the texture image is extracted by using a first network model, and a global feature of the medical images is extracted by using a second network model, so that the network models can focus on the ROI of the medical images, and the extracted features are more precise. In addition, because a fused feature of the global medical feature and the local medical feature is used during image classification, the accuracy of the medical image classification result can be effectively improved.

Figure 6:
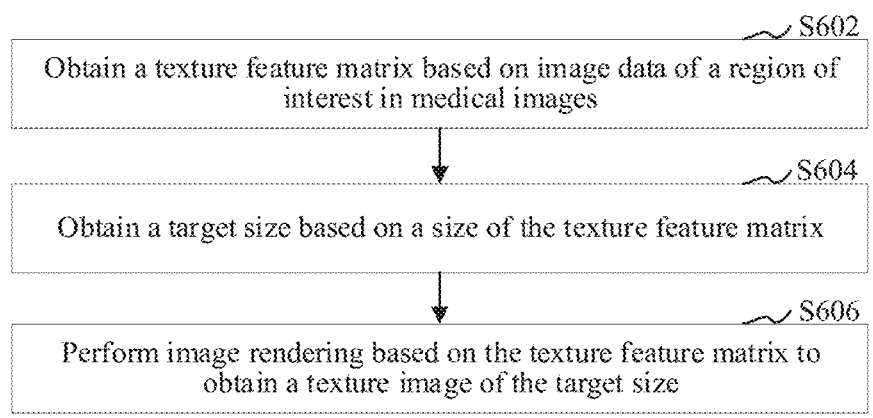
FIG. 6 is a schematic flowchart of steps of generating a texture image according to an embodiment.

In an embodiment, as shown in FIG. 6, S204 may further include:

S602. Obtain a texture feature matrix based on the image data in the ROI in the medical images.

In an embodiment, the terminal obtains any one of the following texture feature matrices from the ROI of the medical images: a GLCM, a GLRLM, a GLSZM, or a GSGM.

In an embodiment, S602 may further include: The terminal obtains pixel values of the medical images, unifies pixel value intervals of the medical images, calculates frequencies at which a target pixel combination appears in the ROI of the medical images and in a target calculation direction, then converts the frequencies into probabilities, to obtain the texture feature matrix. The pixel value interval may be [0, N].

S604. Obtain a target size based on a size of the texture feature matrix.

A smallest resolution unit of the medical images is a pixel. If each medical image has m*n pixels, m representing a length of the image, and n representing a width of the image, a matrix corresponding to the medical image has m rows and n columns. For a texture image, if a texture feature matrix has m rows and n columns, a target size of the texture image is m*n pixels, that is, the texture image is a square with m*n pixels, where m=n. m and n being positive integers.

For example, if pixel values of medical images are unified to a pixel value interval [0, 255], a size of a texture feature matrix is 256*256, and a corresponding target size is 256*256 pixels. In another example, as shown in FIG. 3, if pixel values of medical images are unified to a pixel value interval [1, 8], a size of a texture feature matrix is 8*8, and a corresponding target size is 8*8 pixels.

S606. Perform image rendering based on the texture feature matrix to obtain the texture image of the target size.

Elements in the texture feature matrix are the frequencies at which the target pixel combination appears in the ROI of the medical images and in the target calculation direction, and the frequencies may be used for representing pixel values when generating the texture image based on the texture feature matrix. In an embodiment, the terminal performs image rendering based on the elements in the texture feature matrix to obtain the texture image of the target size.

For a neural network model, if a texture image of an irregular size is inputted (for example, if an inputted texture image is an irregular region image), image classification is affected. Therefore, a texture image of a particular size needs to be generated based on the texture feature matrix, and the texture image is a square.

In an embodiment, the terminal may directly use the texture feature matrix as the texture image without any rendering operation, and input the texture image to the first network model for feature extraction.

In the foregoing embodiments, a texture feature matrix is extracted from the ROI of the medical images, and a texture image of a particular size is generated based on the texture feature matrix, thereby avoiding an impact on the classification result due to an irregular ROI, and improving the accuracy of image classification.

Figure 7:
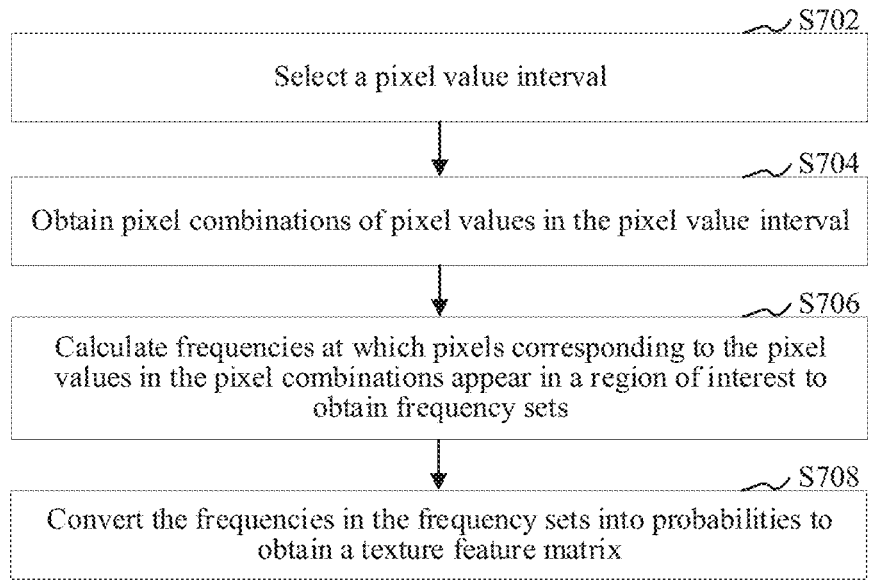
FIG. 7 is a schematic flowchart of steps of obtaining a texture feature matrix according to an embodiment.

In an embodiment, as shown in FIG. 7, S602 may further include:

S702. Select a pixel value interval.

In an embodiment, the terminal sets a pixel value interval based on pixel values of medical images. For example, if the pixel values of the medical images mainly range from 0 to N, the pixel value interval is [0, N].

In an embodiment, when a quantity of obtained medical images that are to be classified is relatively large, the terminal unifies pixel values of the medical images belonging to a same data domain (or a same imaging modality), so that the pixel values of the medical images belonging to the same data domain is within a unified pixel value interval. For example, in CT images, pixel values mainly range from 0 to 50. Therefore, a pixel value greater than 50 in each CT image is converted to a value within the range of 0 to 50, or a pixel value greater than 50 in each CT image is deleted.

S704. Obtain pixel combinations of pixel values in the pixel value interval.

If the pixel value interval is [0, N], a quantity of all possible pixel combinations in the pixel value interval [0, N] is $f(n)=n!=n\times(n-1)\times\ldots\times2\times1$. For example, assuming N=8, the quantity of pixel combinations is $f(n)=8\times7\times\ldots\times2\times1$, such as the quantity of pixel combinations (0, 0), (0, 1), (1, 0), . . . , or (8, 8). The pixel combination may be a combination of two pixel values.

S706. Calculate frequencies at which pixels corresponding to the pixel values in the pixel combinations appear in the ROI to obtain frequency sets.

In an embodiment, S706 may further include: obtaining a target distance and a calculation direction, there being a plurality of calculation directions; obtaining, from the ROI, a pixel meeting the target distance; calculating, based on each of the calculation directions, a quantity of pixels that correspond to pixel values in each of the pixel combinations and that match the pixel meeting the target distance; and obtaining the matching quantity as the frequencies to obtain the plurality of frequency sets corresponding to the quantity of calculation directions. For a two-dimensional single-channel medical image, there may be four calculation directions: a 0° direction, a 45° direction, a 90° direction, and a 145° direction. For a two-dimensional multi-channel medical image, calculation may be respectively performed based on pixel values of different channels. For a three-dimensional single-channel medical image, there may be 13 calculation directions. The target distance generally may be set to 1.

For example, for the two-dimensional single-channel medical image, as shown in FIG. 3, (a) in FIG. 3 shows pixel values in an ROI. A pixel combination GLCM(1, 1) represents a frequency (e.g., a quantity of times, a number of times, a number of counts, etc.) at which pixel values 1 appear in the ROI and in a 0° direction at the same time. The terminal calculates the frequency at which GLCM(1, 1) appears in the ROI and in the 0° direction at the same time. As can be seen from the figure, the frequency at which GLCM(1, 1) appears in the ROI and in the 0° direction at the same time is 0. In this case, 0 is recorded at a corresponding position in (b) in FIG. 3. Similarly, a frequency at which GLCM(8, 4) appears in the ROI and in the 0° direction at the same time is 2. In this case, 2 is recorded at a corresponding position in (b) in FIG. 3. A matrix in (b) in FIG. 3 is obtained after frequencies at which all possible pixel combinations appear in the ROI and in the 0° direction at the same time are calculated. In addition, frequencies at which all the possible pixel combinations appear in the ROI and in 45°, 90°, and 145° directions at the same time are respectively calculated by using the method described above to obtain other three matrices. Frequencies in the obtained four matrices are converted into probabilities. Then, a mean of probabilities at corresponding positions is calculated to obtain a mean matrix. The mean matrix is a texture feature matrix.

S708. Convert frequencies in the frequency sets into probabilities to obtain the texture feature matrix.

The texture feature matrix corresponds to image data in the ROI in the medical images.

In an embodiment, S708 may specifically include: The terminal obtains a quantity of channels of the medical images; converts the frequencies in the plurality of frequency sets into probabilities, and calculates a mean of probabilities after the conversion at corresponding positions in the plurality of frequency sets; obtains, based on the mean of the probabilities, mean probability sets with a quantity consistent with the quantity of channels; and obtains the mean probability sets as the texture feature matrix.

For the image data in the ROI, there are different methods for converting different image data into texture feature matrices:

(1) For a two-dimensional single-channel image, frequency sets in four directions may be directly calculated, frequencies in the frequency sets are converted into probabilities, a mean of the probabilities obtained after conversion in the frequency sets in the four directions is calculated, and the mean is used as an element in a texture feature matrix to obtain the texture feature matrix.

(2) For a two-dimensional multi-channel image such as a two-dimensional multi-modality MRI image or another color image, a frequency set is calculated for each channel, frequencies in the frequency set are converted into probabilities, a mean in frequency sets after the conversion in four directions of each channel is calculated to obtain target frequency sets with a quantity consistent with a quantity of channels, and these target frequency sets are outputted together as a multi-channel texture feature matrix.

(3) For a three-dimensional single-channel isotropic image, frequency sets in 13 directions may be directly calculated, frequencies in the frequency sets are converted into probabilities, a mean of the probabilities obtained after conversion in the frequency sets in the 13 directions is used as an element in a texture feature matrix to obtain the texture feature matrix.

(4) For a three-dimensional single-channel anisotropy image (where an interval in a direction z is excessively large, and resolution is different from that of an xy plane), frequency sets in 4 directions are calculated for each plane, frequencies in the frequency sets are converted into probabilities, then, a mean of the probabilities obtained after conversion in the frequency sets is calculated, and the mean is used as an element in a texture feature matrix to obtain the texture feature matrix.

(5) For a three-dimensional multi-channel image, calculation is performed for each channel according to the rule in (3) or (4) to obtain the texture feature matrix.

In the foregoing embodiments, a pixel value interval is set, frequencies (e.g., a number of times) at which all possible pixel combinations in the pixel value interval appear in the ROI are calculated (e.g., determined). Further, a texture feature matrix used for representing image data of the ROI may be obtained, so as to generate a texture image based on the texture feature matrix, so that a first network model and a second network model focus on the ROI of the medical images. Therefore, extracted features are more precise.

Figure 8:
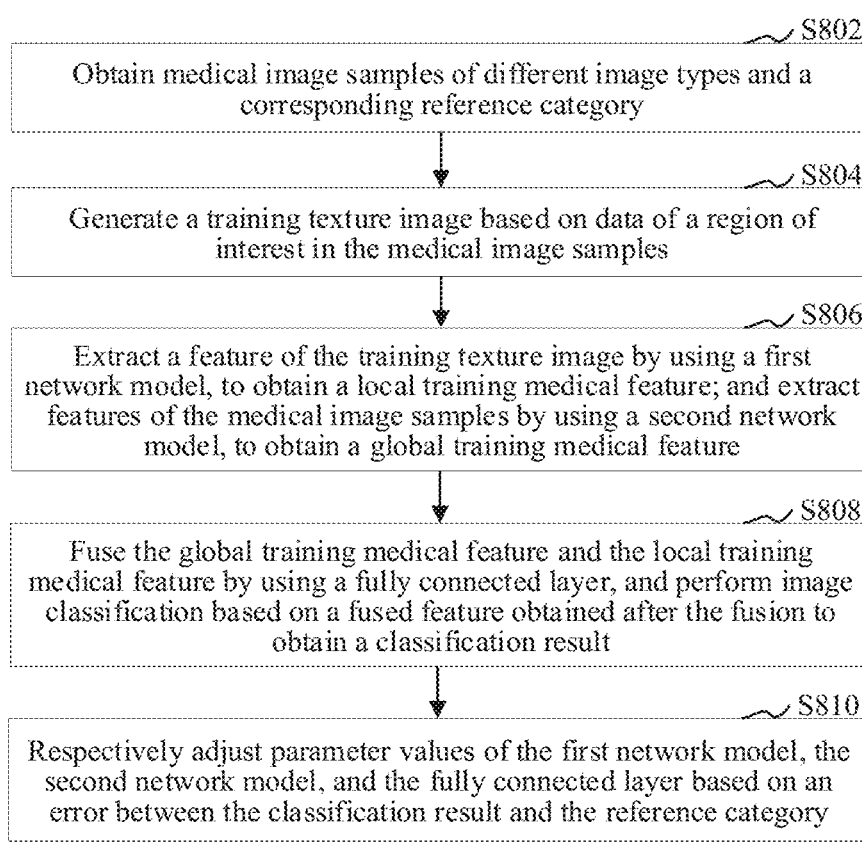
FIG. 8 is a schematic flowchart of steps of training a model including a first network model, a second network model, and a fully connected layer according to an embodiment.

In an embodiment, as shown in FIG. 8, the method may further include:

S802. Obtain medical image samples of different image types and a corresponding reference category.

The medical image samples may be images of different data domains, that is, images of different modalities formed by scanning a human body or a part of a human body by using different medical instruments. Medical image samples obtained in different medical application scenarios belong to different data domains. The data domain may be used for representing that a medical image sample belongs to a medical device or an imaging modality. Different image types correspond to different data domains and different imaging modalities.

For example, the medical image sample may be specifically a CT image obtained by scanning of a CT machine, an MRI image obtained by scanning of an MRI device, or an ultrasound image obtained by scanning of an ultrasound diagnostic instrument. In addition, the medical image sample may alternatively be an X-ray image, an electrocardiogram, an electroencephalogram, or the like. In the medical field, inherent heterogeneity of different symptoms may be reflected in medical image samples. For example, appearances (such as shapes) of a part of human bodies have different degrees of differences. Therefore, medical image samples can be used as a medical judgment method or reference factor to assist clinical diagnosis.

In an embodiment, the terminal selects an instruction based on an inputted image, to select a corresponding medical image sample from an image database; or the terminal establishes a communication connection such as a wired communication connection or a wireless communication connection, to a medical instrument, and obtains, when the medical instrument generates a medical image sample through scanning, the medical image sample generated by the medical instrument.

In an embodiment, after obtaining a medical image sample that is to be classified, the terminal may further perform artifact recognition on the obtained medical image sample to determine whether there is an artifact in the medical image sample and a severity value of the artifact. Alternatively, after obtaining a medical image sample that is to be classified, the terminal outputs the medical image sample for presentation; and when receiving an artifact confirmation instruction for the medical image sample, determines that the medical image sample includes an artifact and a severity value corresponding to the included artifact. If the medical image sample includes an artifact and a severity value of the artifact is relatively large, the terminal may obtain a medical image sample again. If the medical image sample includes an artifact but a severity value of the artifact is relatively small, or the medical image sample includes no artifact, S804 is performed.

S804. Generate a training texture image based on data of an ROI in the medical image samples.

In an embodiment, when no ROI is defined in the obtained medical image samples, the terminal may divide the medical image samples according to an inputted instruction to obtain the ROI, or the terminal may obtain the ROI by learning the ROI by using a machine learning model. In addition, the medical image samples obtained by the terminal may include a defined ROI.

For the ROI, region segmentation may be performed on the medical image samples in the following three manners:

Manner 1: The ROI is obtained by segmentation through supervised learning.

In an embodiment, the medical image samples include segmentation labels, a manner of obtaining the ROI includes: The terminal inputs the medical image samples to an image segmentation network for segmentation, so that a parameter value of the image segmentation network is updated iteratively to obtain a predicted ROI; and inputs the obtained medical image samples to a trained image segmentation network for image segmentation when the predicted ROI matches the segmentation labels, to obtain the ROI of the medical image samples.

The medical image samples may also be images of different data domains, that is, images of different modalities formed by scanning a human body or a part of a human body by using different medical instruments.

In an embodiment, the step of inputting the obtained medical image samples to a trained image segmentation network for image segmentation to obtain the ROI of the medical image samples may include: The terminal inputs the obtained medical image samples to the trained image segmentation network; performs feature extraction on the medical image samples by using the image segmentation network, to obtain an image feature of a target object in the medical image samples; and inputs the obtained image feature to the image segmentation network for processing, to obtain the ROI.

For example, the terminal obtains medical image samples having segmentation labels, then trains an image segmentation network by using the medical image samples having the segmentation labels, and obtains a trained image segmentation network when an output of the image segmentation network gradually becomes stable (in other words, when an obtained ROI is consistent with the segmentation labels). Then, the terminal inputs the obtained medical image samples to the trained image segmentation network for image segmentation, to obtain the ROI of the medical image samples.

In another example, when the number of obtained medical image samples is relatively large, some of the medical image samples may be marked to obtain medical image samples having segmentation labels. Then, an image segmentation network is trained by using the medical image samples having the segmentation labels, and a trained image segmentation network is obtained when an output of the image segmentation network gradually becomes stable (in other words, when an obtained ROI is consistent with the segmentation labels). The terminal inputs the obtained medical image samples that are not marked to the trained image segmentation network for image segmentation, to obtain the ROI of the medical image samples.

Manner 2: The ROI is obtained by segmentation through unsupervised learning.

In an embodiment, a manner of obtaining the ROI includes: The terminal obtains pixel values of the medical image samples, and obtains, when the pixel values meet a target condition, a region corresponding to the pixel values meeting the target condition as the ROI.

Manner 3: The ROI is obtained by segmentation manually.

In an embodiment, a manner of obtaining the ROI includes: The terminal obtains an inputted ROI definition instruction, and defines an ROI corresponding to the ROI definition instruction in the medical image samples.

For example, when the number of medical image samples is relatively small, the ROI may be defined through manual marking. When receiving an ROI definition instruction (for example, drawing on medical image samples displayed on the terminal) issued by a doctor or other technical personnel, the terminal draws an ROI corresponding to the ROI definition instruction in the medical image samples.

In an embodiment, the terminal extracts a texture feature matrix from the ROI of the medical image samples. The texture feature matrix may be any one of a GLCM, a GLRLM, a GLSZM, or a GSGM.

In an embodiment, the step of extracting a texture feature matrix from the ROI of the medical image samples may specifically include: The terminal first unifies pixel value intervals of the medical image samples, and then calculates frequencies at which a target pixel combination appears in the ROI of the medical image samples and in a target calculation direction, to obtain the texture feature matrix. The pixel value interval may be [0, N].

S806. Extract a feature of the training texture image by using a first network model, to obtain a local training medical feature; and extract features of the medical image samples by using a second network model, to obtain a global training medical feature.

The first network model may be a network branch in a deep learning network model, the network branch may belong to the VGG network, the Inception network, the ResNet network, the DenseNet network, or the like; or may be formed by a plurality of network layers (for example, a convolutional layer and a pooling layer) of the foregoing networks, the layers being configured to extract a local medical feature. Because a texture image is generated by the image data of the ROI in the medical images, the feature extracted based on the texture image may be referred to as the local medical feature. The second network model may be another network branch in the deep learning network model, in other words, the deep learning network model includes the first network model and further includes the second network model. The second network model may also belong to the VGG network, the Inception network, the ResNet network, the DenseNet network, or the like; or may be formed by a plurality of network layers (for example, a convolutional layer and a pooling layer) in the foregoing networks, the layers being configured to extract a global medical feature, that is, extract another medical feature outside the ROI in the medical images in addition to a medical feature in the ROI. In addition, the deep learning network model further includes a fully connected layer configured to fuse the features extracted by the first network model and the second network model, so as to perform image classification by using a fused feature.

The first network model may include a plurality of convolutional layers and at least one pooling layer. In an embodiment, the terminal performs convolution processing on the texture image by using the convolutional layers in the first network model, for example, performs convolution processing on an inputted texture image by using a first convolutional layer, and performs convolution processing on an output result of the first convolutional layer as an input by using a second convolutional layer, and the rest may be deducted by analogy. After performing convolution processing by using the convolutional layers in the first network model, the terminal performs pooling processing on a result obtained after the convolution processing. A result obtained after the pooling processing is the local training medical feature.

The second network model may include convolutional layers and a pooling layer. In an embodiment, the terminal performs convolution processing on the medical images by using the convolutional layers in the second network model, for example, performs convolution processing on inputted medical images by using a first convolutional layer, and performs convolution processing on an output result of the first convolutional layer as an input by using a second convolutional layer, and the rest may be deducted by analogy, to obtain a final convolution. After performing convolution processing by using the convolutional layers in the second network model, the terminal performs pooling processing on a result obtained after the convolution processing. A result obtained after the pooling processing is the global training medical feature.

S808. Fuse the global training medical feature and the local training medical feature by using a fully connected layer, and perform image classification based on a fused feature obtained after the fusion to obtain a classification result.

In an embodiment, the terminal fuses the global training medical feature and the local training medical feature by using the fully connected layer in the deep learning network model, to obtain a fused feature; and then, performs image classification on the medical image samples based on the fused feature.

In an embodiment, S808 may further include: The terminal fuses the global training medical feature and the local training medical feature by using the fully connected layer, to obtain the fused feature; performs convolution calculation on the fused feature; and performs image classification on the medical image samples based on a result obtained after the convolution calculation.

For example, as shown in Table 2, if a feature size of the global training medical feature is 1024 and a feature size of the local training medical feature is 32, the global training medical feature and the local training medical feature are fused by using the fully connected layer, to obtain a fused feature having a feature size of 1024+32. Then, convolution processing is performed on the fused feature by using the fully connected layer, to obtain a vector with four elements. The elements in the vector are used for representing probabilities (or proportions) that a medical image sample belongs to corresponding types. Then, a type corresponding to the largest probability is used as a target type of the medical image sample. The target type may be represented by a number. For example, 0 represents a type A, 1 represents a type B, 2 represents a type C, and 3 represents a type D.

In an example, as shown in FIG. 4, after medical image samples are obtained, a texture feature matrix (for example, a GLCM) is extracted from an ROI in the medical image samples, and the texture feature matrix is mapped to an image of a same size to obtain a texture image. The texture image is inputted to a first network model (that is, a CNN model 1) of a deep learning network model for feature extraction, to obtain a local training medical feature $f_{j1}$, $f_{j2}$, ..., $f_{jm}$. The medical image samples are inputted to a second network model (that is, a CNN model 2) of the deep learning network model for feature extraction, to obtain a global training medical feature $f_{i1}$, $f_{i2}$, ..., $f_{in}$. The local training medical feature $f_{j1}$, $f_{j2}$, ..., $f_{jm}$ and the global training medical feature $f_{i1}$, $f_{i2}$, ..., $f_{in}$ are fused by using a fully connected layer, to obtain a fused feature $f_{i1}$, $f_{i2}$, ... $f_{in}$, $f_{j1}$, $f_{j2}$, ..., $f_{jm}$. Then, the fused feature is processed to obtain a classification result.

S810. Respectively adjust parameter values of the first network model, the second network model, and the fully connected layer based on an error between the classification result and the reference category.

In an embodiment, S810 may further include: The terminal obtains the error between the classification result and the reference category; back-propagates the error to neurons of the first network model, the second network model, and the fully connected layer to obtain a gradient of parameter values of the neurons; and updates the parameter values of the neurons based on the gradient.

In an embodiment, the terminal updates the parameter values of the neurons of the first network model, the second network model, and the fully connected layer by using an Adam-based gradient descent method. Specifically, the method used by the terminal includes but is not limited to gradient descent methods such as an Adam gradient descent method, a stochastic gradient descent (SGD) method, a mini-batch gradient descent (MBGD) method, and a batch gradient descent (BGC) method. Learning rates of a first-order moment estimation and a second-order moment estimation of each parameter value gradient are dynamically adjusted based on an error calculated by using a loss function. Because the Adam gradient descent method has a determined range for a learning stride of each iteration parameter, a large learning stride does not occur due to a relatively large gradient, and a parameter value is relatively stable.

In an embodiment, the terminal may calculate the error between the classification result and the reference category by using the following loss functions: a mean square error loss function, a cross entropy function, a support vector machine (SVM) hinge loss function, and a smooth L1 loss function. The foregoing loss functions are merely examples and are not exhaustive, but this application is not limited to the foregoing loss functions.

In the foregoing embodiments, a first network model, a second network model, and a fully connected layer are trained by using medical image samples of different image types and a training texture image generated based on data of an ROI, to obtain a deep learning network model that includes the first network model, the second network model, and the fully connected layer and that is used for image classification. Because the network models are obtained through training by using a texture image generated based on the image data of the ROI in the medical images, the network models focus on the ROI of the medical images, so that the extracted features are more precise, thereby effectively improving the accuracy of the medical image classification result.

Figure 9:
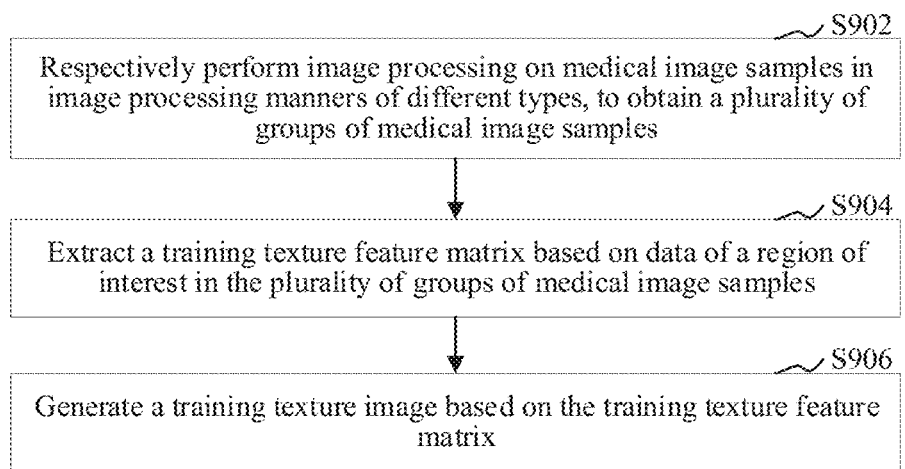
FIG. 9 is a schematic flowchart of steps of increasing medical image samples and obtaining a training texture image according to an embodiment.

In an embodiment, as shown in FIG. 9, the method may further include:

S902. Respectively perform image processing on the medical image samples in image processing manner of different types, to obtain a plurality of groups of medical image samples.

The image processing manners include rotation, scaling, brightness adjustment, and image contrast enhancement of the medical image samples. The image contrast enhancement may be implemented by adjusting pixel values of medical image samples by using a cumulative function.

Because a medical image sample generally has no ROI (for example, a lesion region) with a fixed shape, size, or directionality, additional processing (e.g., image processing), such as rotation, scaling, brightness adjustment, and image contrast enhancement need to be performed on the medical image sample to increase the number of medical image samples and increase the directionality and a value of information under different scales.

In an embodiment, the terminal rotates a medical image sample to obtain a plurality of medical image samples with different rotation angles. The terminal scales a medical image sample to obtain medical image samples with different scaling ratios. The terminal performs brightness adjustment on a medical image sample to obtain medical image samples with different brightness. The terminal performs image contrast enhancement on a medical image sample to obtain medical image samples with different contrasts. Medical images are processed in the foregoing image processing manners of different types to obtain a plurality of groups of medical image samples. The plurality of groups of medical image samples include original medical image samples.

In some embodiments, S804 may further include: S904. Extract a training texture feature matrix based on the data of the ROI in the plurality of groups of medical image samples.

In an embodiment, the step of extracting a training texture feature matrix from the ROI of the plurality of groups of medical image samples may specifically include: The terminal first unifies pixel value intervals of the plurality of groups of medical image samples, and then calculates frequency at which a target pixel combination appears in the ROI of the plurality of groups of medical image samples and in a target calculation direction, to obtain the training texture feature matrix. The pixel value interval may be [0, N].

S906. Generate a training texture image based on the training texture feature matrix.

Elements in the training texture feature matrix are the frequencies at which the target pixel combination appears in the ROI of the plurality of groups of medical images and in the target calculation direction, and the frequencies may be used for representing pixel values when generating the training texture image based on the training texture feature matrix. In an embodiment, the terminal performs image rendering based on the elements in the training texture feature matrix to obtain the texture image of a target size.

A smallest resolution unit of the texture image is a pixel. If the texture feature matrix has m rows and n columns, the target size of the texture image is m*n pixels, that is, the texture image is a square with m*n pixels, where m=n.

For a neural network model, if a training texture image of an irregular size is inputted (for example, if an inputted training texture image is an irregular region image), image classification is affected. Therefore, a training texture image of a particular size needs to be generated based on the training texture feature matrix. The training texture image is a square.

In the foregoing embodiments, image processing is performed on medical image samples respectively in image processing manners of different types, to increase a quantity (e.g., number) of medical image samples. Neurons of the first network model, the second network model, and the fully connected layer are obtained through training by using the processed medical image samples. Therefore, calculation performance of the first network model, the second network model, and the fully connected layer can be generalized, and medical images of a plurality of image sizes, directions, brightness, and contrasts can be classified, facilitating improvement of the accuracy of image classification.

Figure 10:
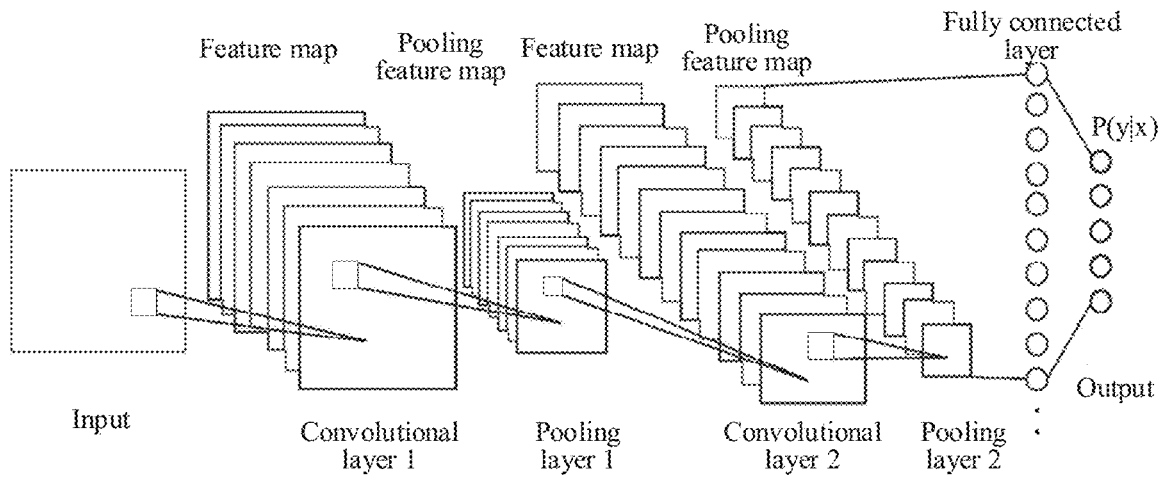
FIG. 10 is a schematic diagram of classifying medical images by using a CNN model according to an embodiment.

In an example, conventional medical image classification solutions mainly include:

(1) A DCNN-based classification network technology: As shown in FIG. 10, classification is implemented through a series of convolution and pooling operations, different features are extracted by using a series of convolution kernels, and an optimal parameter is found through a loss function and back-propagation, to implement feature selection and image classification, and obtain a classification result when the loss function is minimized.

Because a DCNN model is a neural network-based classification model, features learned by using this method are all at a gray value level, and an inputted image of a neural network needs to be a patch not an irregular region (for example, a segmented region drawn by a doctor), a large quantity of non-segmented regions as lesion-free regions affects a classification result. Especially for a small lesion, the DCNN model may not focus on the lesion and miss lesion information.

Figure 11:
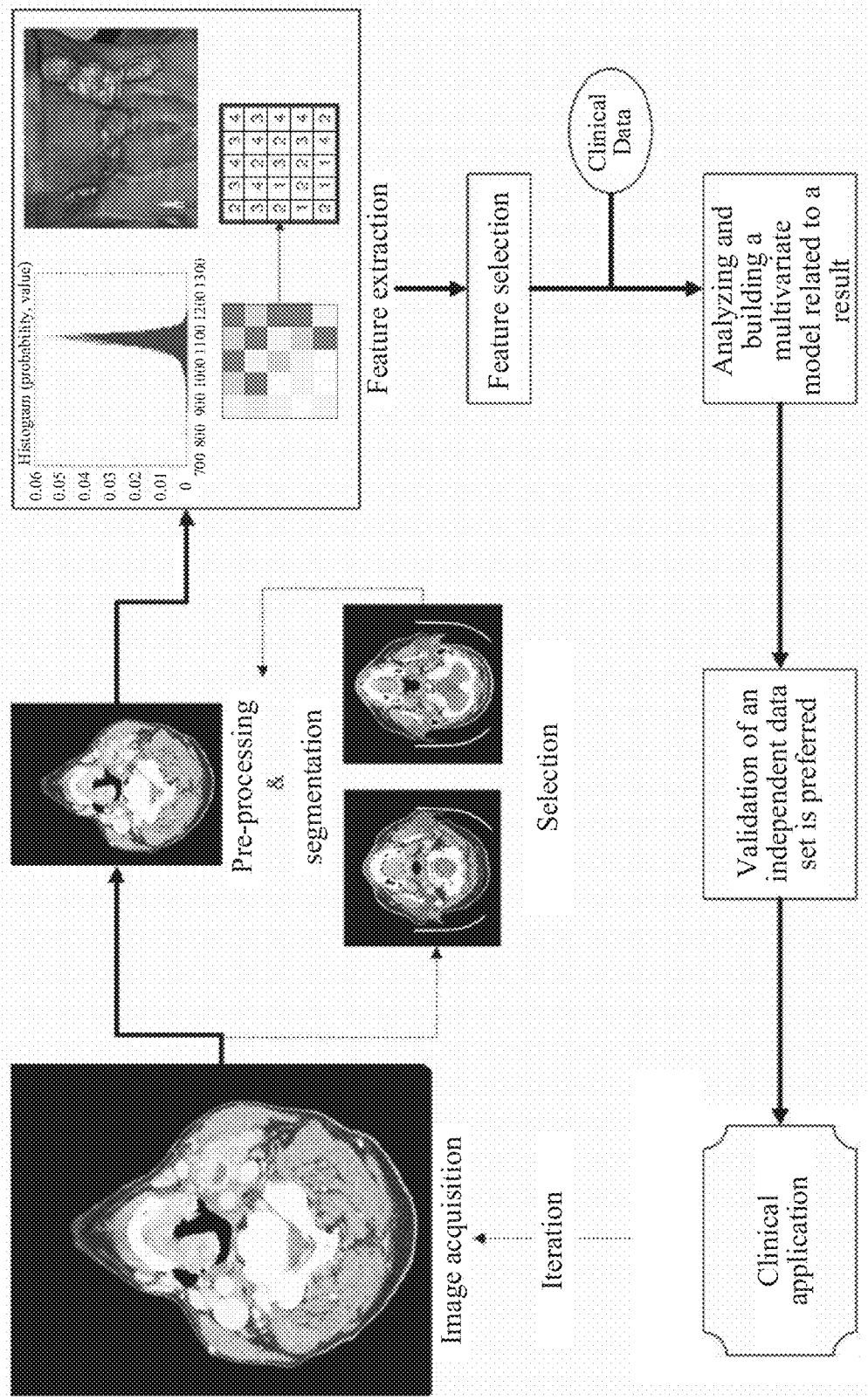
FIG. 11 is a schematic diagram of classifying medical images by using a DCNN model according to an embodiment.

(2) A conventional feature is extracted from a medical image or an ROI. Then, image classification is implemented by using a classifier such as an SVM, as shown in FIG. 11.

There are several problems if a feature is extracted from an ROI or an entire medical image in a manner of manually designing a feature. First, manual features may not be an optimal solution in the mathematical sense, and therefore, cannot represent most meaningful features, and further affect a classification result. Second, relatively strong correlations between information of the manual features may result in overfitting. Therefore, an extra feature selection algorithm is required to select a most useful feature set. Third, the manual features are extracted from an ROI, and cannot reflect global information such as an association between other regions and the ROI.

To resolve the foregoing problems, the embodiments of this application provide an image classification solution, which is described with reference to FIG. 5. Details are as follows:

(I) Application Phase:

(1) Obtaining medical images.

(2) Mark an ROI on the medical images.

There may be three manners of obtaining the ROI: First, a doctor draws or marks a lesion region. Second, some medical images are segmented and marked, then, an image segmentation model is trained by using the marked medical images, and unmarked medical images are inputted to a trained image segmentation network model for segmentation to obtain the ROI. Third, a lesion region is obtained through segmentation by using a gray value feature of the lesion region and an unsupervised algorithm. For example, when a gray value is greater than a threshold, a region corresponding to the gray value greater than the threshold is used as the ROI.

(3) Extract a GLCM from the ROI to obtain a two-dimensional image for the ROI.

First, image gray values are unified to [0, N]. Then, the GLCM is extracted from the ROI. The GLCM is obtained by collecting statistics about gray values of two adjacent pixels of an image in a direction, where there is a distance between the two adjacent pixels, and the distance is usually set to 1. Therefore, as shown in FIG. 3, a value in the second row and the second column in the GLCM is a frequency at which a pair of gray values (2, 2) of two pixels appear in the ROI and in a 0° direction, where a distance between the two pixels is 1, and the frequency at which the gray values (2, 2) appear in (a) in FIG. 3 is 1; and a value in the second row and the third column in the GLCM is a frequency at which gray values (2, 3) appear in the ROI and in the 0° direction, and the frequency is 1. Finally, (b) in FIG. 3 is converted into a probability plot, to be specific, the matrix is divided by a sum of all elements in the matrix.

A GLCM may be extracted from a two-dimensional image in four directions, and may be extracted from a three-dimensional image in 13 directions. A method for manually calculating a feature by using values in the GLCM in a conventional solution is shown as follows:

$$GLCM: \begin{bmatrix} p_{11} & p_{12} & \cdots & p_{1n} \\ p_{21} & p_{21} & \cdots & p_{2n} \\ \vdots & \vdots & \ddots & \vdots \\ p_{n1} & p_{n1} & \cdots & p_{nn} \end{bmatrix}$$

$$\text{Feature 1: Contrast} = \sum_{n=1}^{N-1} p_{ij}(i-j)^2$$

$$\text{Feature 2: Homogeneity} = \sum_{n=1}^{N-1} \frac{p_{ij}}{1+(i-j)^2}$$

As can be learned, the foregoing features are linear combinations of elements in the GLCM, and coefficients are fixed (related to i and j). The following problems exist: Manually calculated features may not be an optimal solution in the mathematical sense, and therefore, affect a classification result; and relatively strong correlations between the features may cause overfitting.

Therefore, in this solution, a two-dimensional image is formed by the GLCM after processing of the DCNN model. As such, features obtained by using this solution are better than features obtained by using fixed coefficients.

(4) The medical images and a two-dimensional image about the ROI are inputted to the DCNN model for image classification to obtain a classification result.

As shown in FIG. 4, a two-dimensional image formed based on a GLCM is inputted to a CNN model 1 for feature extraction to obtain a local medical feature; and medical images are inputted to a CNN model 2 for feature extraction to obtain a global medical feature. Then, the global medical feature and the local medical feature are fused by using a fully connected layer, to obtain a fused feature. The fused feature is processed, and a classification result is inputted.

(II) Training Phase:

In the embodiments of this application, the following three types of data sets are obtained as medical image samples to train the DCNN model: First, a CT plain scan brain hemorrhage cause judgment data set, second, an MRI data set including four modalities, and third, a three-channel cervical color image staging data set.

(1) Construct Training Data

Obtained medical image samples are normalized, so that the obtained medical image samples are in the interval [0, 1]. Data augmentation operations such as flipping, rotation, scaling, and contrast enhancement are performed on the medical image samples to increase a quantity of training samples, increase the directionality and a value of information under different scales.

For data of the ROI, different data may be converted into GLCMs in different processing manners:

First, for a two-dimensional single-channel image, a mean of GLCMs in four directions is directly extracted as a GLCM.

Second, for a two-dimensional multi-channel image such as a two-dimensional multi-modality MR image or a color image, a GLCM is extracted for each channel. Then, all GLCMs are outputted together as a multi-channel GLCM.

Third, for a three-dimensional single-channel isotropic image, a mean of GLCMs in 13 directions is extracted as a GLCM.

Four, for a three-dimensional single-channel anisotropy image (where an interval in a direction z is excessively large, and resolution is different from that of an xy plane), four GLCMs are calculated for each xy plane, and a mean of all calculated GLCMs is calculated.

Five, for a three-dimensional multi-channel image, calculation is performed for each channel according to the foregoing rules, and a multi-channel GLCM is outputted.

(2) Design a Deep Learning Network Model

First, Basic Module Design

As shown in FIG. 4, for the CNN model 2, a part of network from the first layer of an existing classic network to a fully connected layer at which an input ends is used as the CNN model 2. The classic network may include but is not limited to: VGG16, ResNet18, ResNet50, InceptionV3, and the like.

Second, Entire Network Design

As shown in FIG. 4, the entire network includes two branches: the CNN model 1 and the CNN model 2. Advantages of the two branch networks are combined into the DCNN model. The CNN model 2 mainly searches entire medical images for a feature of a key region (including but not limited to an ROI). The CNN model 1 can focus on a feature of the ROI, and therefore, can force the DCNN model to pay attention to the ROI, so that an extracted feature is more precise. Experiments show that the CNN model 1 extracts, by using two-dimensional (2D) ResNet, a feature in a two-dimensional image formed based on the GLCM. This has a good effect.

A difference between the CNN model 1 and ResNet18 is that one ResNet block is reduced in the CNN model 1, and a quantity of output channels after each convolutional layer is also reduced. Because only 32 features are extracted by using the CNN model 1, only a relatively narrow and shallow network is required to complete the extraction, thereby improving the classification accuracy.

Features of two branches are fused at the fully connected layer of the network, and there are 1024+32 features in total. Then, an output is a quantity of categories (for example, Table 2 shows 4 categories of cerebral hemorrhage data).

(3) Deep Learning Network Model Training

In the embodiments of this application, a parameter of a network is updated by using an Adam-based gradient descent method. Before a model is trained, a two-dimensional image formed by a GLCM is first obtained by using the method for constructing training data in the foregoing step (1). Then, original medical image samples and the two-dimensional image formed by the GLCM are inputted to the deep learning network model. A predicted category (an N*1 vector, where N is a quantity of categories) is obtained by using the deep learning network model. A cross entropy between the predicted category and a label (that is, an actual category) is calculated as a loss function. An error gradient may be calculated by minimizing the loss function, and a gradient of the network may be updated through back-propagation. Finally, the trained deep learning network model is obtained.

By implementing the foregoing embodiment, the following technical effects can be achieved:

(1) Compared with classification based on conventional feature classification or only DCNN-based classification, the classification accuracy is improved.

(2) The foregoing technical solution can be applied to a plurality of types of medical images.

(3) The foregoing technical solution can be combined with a plurality of DCNN models to generate algorithms.

(4) An optimization algorithm of a DCNN model is used together with a conventional feature extraction method, so that a conventional feature and a depth feature are organically combined.

FIG. 2, FIG. 6 to FIG. 9 are schematic flowcharts of an image classification method according to an embodiment. It is to be understood that, although each step of the flowcharts in FIG. 2, FIG. 6 to FIG. 9 is displayed sequentially according to arrows, the steps are not necessarily performed according to an order indicated by arrows. Unless clearly specified in this specification, there is no strict sequence limitation on the execution of the steps, and the steps may be performed in another sequence. Moreover, at least part of the steps in FIG. 2, FIG. 6 to FIG. 9 may include a plurality of sub-steps or a plurality of stages. These sub-steps or stages are not necessarily executed at the same time, but can be executed at different times. The order of execution of these sub-steps or stages is not necessarily performed sequentially, but may be performed in turn or alternately with other steps or at least a part of sub-steps or stages of other steps.

Figure 12:
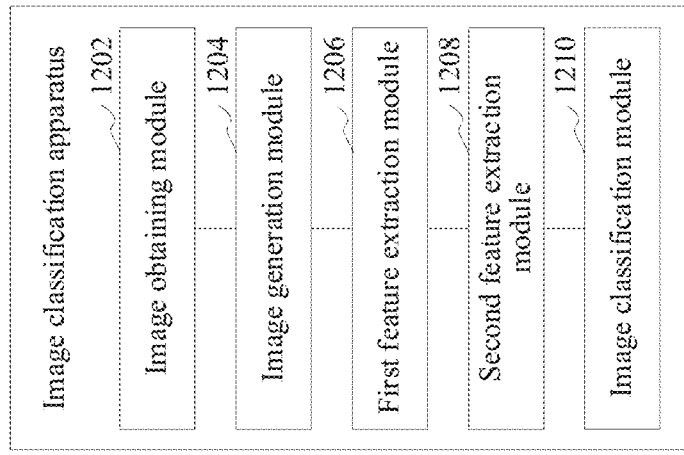
FIG. 12 is a structural block diagram of an image classification apparatus according to an embodiment.

As shown in FIG. 12, in an embodiment, an image classification apparatus is provided. The apparatus includes: an image obtaining module 1202, an image generation module 1204, a first feature extraction module 1206, a second feature extraction module 1208, and an image classification module 1210.

The image obtaining module 1202 is configured to obtain medical images that are to be classified.

The image generation module 1204 is configured to generate a texture image based on image data of an ROI in the medical images.

The first feature extraction module 1206 is configured to perform feature extraction on the texture image by using a first network model, to obtain a local medical feature.

The second feature extraction module 1208 is configured to perform feature extraction on the medical images by using a second network model, to obtain a global medical feature.

The image classification module 1210 is configured to perform image classification based on a fused feature of the global medical feature and the local medical feature.

Figure 13:
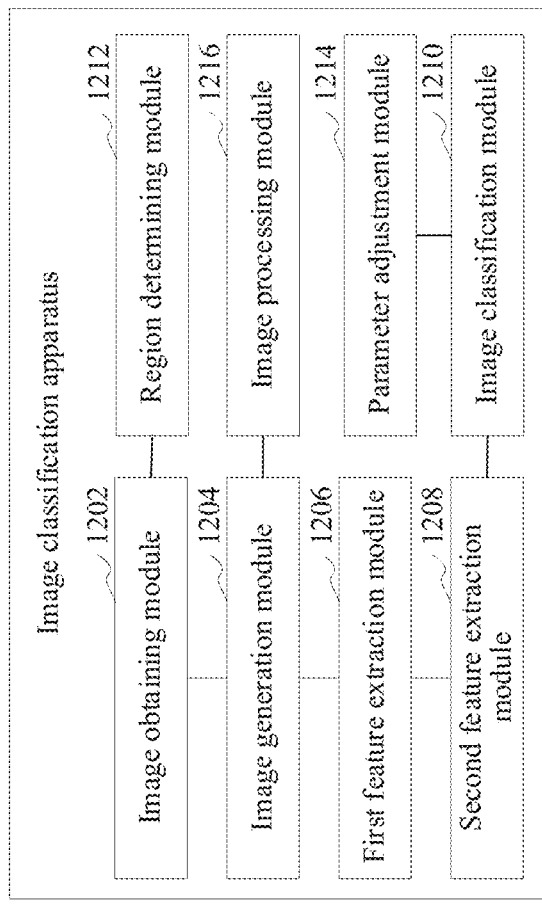
FIG. 13 is a structural block diagram of an image classification apparatus according to another embodiment.

In an embodiment, as shown in FIG. 13, the apparatus further includes a region obtaining module 1212.

The region obtaining module 1212 is configured to obtain medical image samples having segmentation labels; input the medical image samples to an image segmentation network for segmentation to obtain a predicted ROI; and input the obtained medical images to a trained image segmentation network for image segmentation when the predicted ROI matches the segmentation labels, to obtain the ROI of the medical images.

In an embodiment, the region obtaining module 1212 is further configured to obtain an inputted ROI definition instruction, and define a ROI corresponding to the ROI definition instruction in the medical images; or obtain pixel values of the medical images, and obtain, when the pixel values meet a target condition, a region corresponding to the pixel values meeting the target condition as the ROI.

In an embodiment, the image classification module 1210 is further configured to: fuse the global medical feature and the local medical feature by using a fully connected layer, to obtain the fused feature; perform convolution calculation on the fused feature; and perform image classification on the medical images based on a result obtained after the convolution calculation.

In the foregoing embodiments, a texture image is generated by using image data of an ROI in medical images. Then, a local feature of the texture image is extracted by using a first network model, and a global feature of the medical images is extracted by using a second network model, so that the network models can focus on the ROI of the medical images, and the extracted features are more precise. In addition, because a fused feature of the global medical feature and the local medical feature is used during image classification, the accuracy of the medical image classification result can be effectively improved.

In an embodiment, the image generation module 1204 is further configured to obtain a texture feature matrix based on the image data in the ROI in the medical images, obtain a target size based on a size of the texture feature matrix, and perform image rendering based on the texture feature matrix to obtain the texture image of the target size.

In the foregoing embodiments, a texture feature matrix is extracted from the ROI of the medical images, and a texture image of a particular size is generated based on the texture feature matrix, thereby avoiding an impact on the classification result due to an irregular ROI, and improving the accuracy of image classification.

In an embodiment, the image generation module 1204 is further configured to select a pixel value interval, obtain pixel combinations of pixel values in the pixel value interval, calculate frequencies at which pixels corresponding to the pixel values in the pixel combinations appear in the ROI to obtain frequency sets, and convert frequencies in the frequency sets into probabilities to obtain the texture feature matrix.

In an embodiment, the image generation module 1204 is further configured to obtain a target distance and a calculation direction, there being a plurality of calculation directions; obtain, from the ROI, a pixel meeting the target distance; calculate, based on each of the calculation directions, a quantity of pixels that correspond to pixel values in each of the pixel combinations and that match the pixel meeting the target distance; and obtain the matching quantity as the frequencies to obtain the plurality of frequency sets corresponding to a quantity of the calculation directions.

In an embodiment, the image generation module 1204 is further configured to obtain a quantity of channels of the medical images; convert the frequencies in the plurality of frequency sets into probabilities, and calculate a mean of probabilities obtained after the conversion at corresponding positions in the plurality of frequency sets; obtain, based on the mean of the probabilities, mean probability sets with a quantity consistent with the quantity of channels; and obtain the mean probability sets as the texture feature matrix.

In the foregoing embodiments, a pixel value interval is set, frequencies at which all possible pixel combinations in the pixel value interval appear in the ROI are calculated. Further, a texture feature matrix used for representing image data of the ROI is obtained, so as to generate a texture image based on the texture feature matrix, so that a first network model and a second network model focus on the ROI of the medical images. Therefore, extracted features are more precise.

In an embodiment, as shown in FIG. 13, the apparatus further includes a parameter adjustment module 1214.

The image obtaining module 1202 is further configured to obtain medical image samples of different image types and a corresponding reference category.

The image generation module 1204 is further configured to generate a training texture image based on data of an ROI in the medical image samples.

The first feature extraction module 1206 is further configured to extract a feature of the training texture image by using the first network model, to obtain a local training medical feature.

The second feature extraction module 1208 is further configured to extract features of the medical image samples by using the second network model, to obtain a global training medical feature.

The image classification module 1210 is further configured to fuse the global training medical feature and the local training medical feature by using the fully connected layer, and perform image classification based on a fused feature obtained after the fusion to obtain a classification result.

The parameter adjustment module 1214 is configured to separately adjust parameter values of the first network model, the second network model, and the fully connected layer based on an error between the classification result and the reference category.

In the foregoing embodiments, a first network model, a second network model, and a fully connected layer are trained by using medical image samples of different image types and a training texture image generated based on data of an ROI, to obtain a deep learning network model that includes the first network model, the second network model, and the fully connected layer and that is used for image classification. Because the network models are obtained through training by using the texture image generated based on the image data of the ROI in the medical images, the network models focus on the ROI of the medical images, so that the extracted features are more precise, thereby effectively improving the accuracy of the medical image classification result.

In an embodiment, the parameter adjustment module 1214 is further configured to obtain the error between the classification result and the reference category; back-propagate the error to neurons of the first network model, the second network model, and the fully connected layer to obtain a gradient of parameter values of the neurons; and update the parameter values of the neurons based on the gradient.

In an embodiment, as shown in FIG. 13, the apparatus further includes an image processing module 1216.

The image processing module 1216 is configured to respectively perform image processing on the medical image samples in image processing manners of different types, to obtain a plurality of groups of medical image samples.

The image generation module 1204 is further configured to extract a training texture feature matrix based on the data of the ROI in the plurality of groups of medical image samples; and generate a training texture image based on the training texture feature matrix.

In the foregoing embodiments, image processing is respectively performed on medical image samples in image processing manners of different types, to increase a quantity of medical image samples. Neurons of the first network model, the second network model, and the fully connected layer are obtained through training by using the processed medical image samples. Therefore, calculation performance of the first network model, the second network model, and the fully connected layer can be generalized, and medical images of a plurality of image sizes, directions, brightness, and contrasts can be classified, facilitating improvement of the accuracy of image classification.

Figure 14:
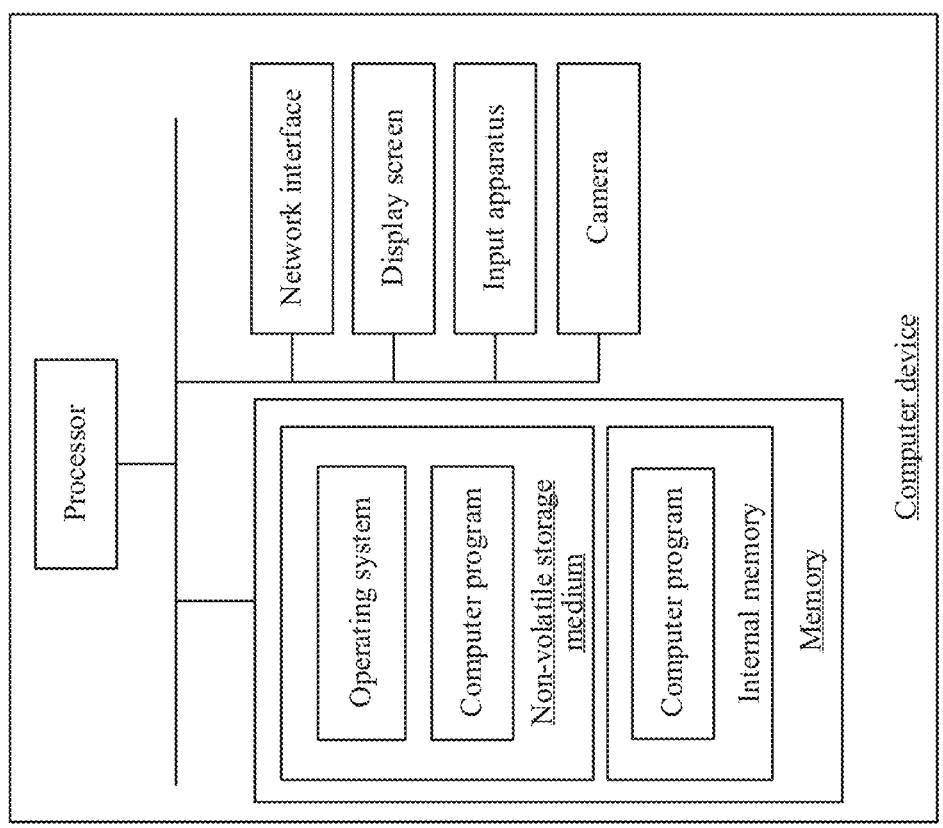
FIG. 14 is a structural block diagram of a computer device according to an embodiment.

FIG. 14 is a diagram of an internal structure of a computer device in an embodiment. The computer device may be specifically the terminal 110 in FIG. 1. As shown in FIG. 14, the computer device includes a processor, a memory, a network interface, an input apparatus, and a display screen that are connected by a system bus. The memory includes a non-volatile storage medium and an internal memory. The non-volatile storage medium of the computer device stores an operating system and may further store a computer program, the computer program, when executed by the processor, causing the processor to implement the image classification method. The internal memory may also store a computer program. The computer program, when executed by the processor, may cause the processor to perform the following steps:

obtaining medical images that are to be classified; generating a texture image based on image data of an ROI in the medical images; performing feature extraction on the texture image by using a first network model, to obtain a local medical feature; performing feature extraction on the medical images by using a second network model, to obtain a global medical feature; and performing image classification based on a fused feature of the global medical feature and the local medical feature.

In an embodiment, the computer program, when executed by the processor, causes the processor to perform the following steps:

obtaining medical image samples having segmentation labels; inputting the medical image samples to an image segmentation network for segmentation to obtain a predicted ROI; and inputting the obtained medical images to a trained image segmentation network for image segmentation when the predicted ROI matches the segmentation labels, to obtain the ROI of the medical images.

In an embodiment, the computer program, when executed by the processor, causes the processor to perform the following steps:

obtaining an inputted ROI definition instruction, and defining an ROI corresponding to the ROI definition instruction in the medical images; or obtaining pixel values of the medical images, and obtaining, when the pixel values meet a target condition, a region corresponding to the pixel values meeting the target condition as the ROI.

In an embodiment, the computer program, when executed by the processor, causes the processor to perform the following steps:

obtaining a texture feature matrix based on the image data of the ROI in the medical images, obtaining a target size based on a size of the texture feature matrix, and performing image rendering based on the texture feature matrix to obtain the texture image of the target size.

In an embodiment, the computer program, when executed by the processor, causes the processor to perform the following steps:

selecting a pixel value interval, obtaining pixel combinations of pixel values in the pixel value interval, calculating frequencies at which pixels corresponding to the pixel values in the pixel combinations appear in the ROI to obtain frequency sets, and converting the frequencies in the frequency sets into probabilities to obtain the texture feature matrix.

In an embodiment, the computer program, when executed by the processor, causes the processor to perform the following steps:

obtaining a target distance and a calculation direction, there being a plurality of calculation directions; obtaining, from the ROI, a pixel meeting the target distance; calculating, based on each of the calculation directions, a quantity of pixels that correspond to pixel values in each of the pixel combinations and that match the pixel meeting the target distance; and obtaining the matching quantity as the frequencies to obtain the plurality of frequency sets corresponding to a quantity of the calculation directions.

In an embodiment, the computer program, when executed by the processor, causes the processor to perform the following steps:

obtaining a quantity of channels of the medical images; converting the frequencies in the plurality of frequency sets into probabilities, and calculating a mean of probabilities at corresponding positions in the plurality of frequency sets; obtaining, based on the mean of the probabilities, mean probability sets with a quantity consistent with the quantity of channels; and obtaining the mean probability sets as the texture feature matrix.

In an embodiment, the computer program, when executed by the processor, causes the processor to perform the following steps:

fusing the global medical feature and the local medical feature by using a fully connected layer, to obtain the fused feature; performing convolution calculation on the fused feature; and performing image classification on the medical images based on a result obtained after the convolution calculation.

In an embodiment, the computer program, when executed by the processor, causes the processor to perform the following steps:

obtaining medical image samples of different image types and a corresponding reference category; generating a training texture image based on data of an ROI in the medical image samples; extracting a feature of the training texture image by using the first network model, to obtain a local training medical feature; extracting features of the medical image samples by using the second network model, to obtain a global training medical feature; fusing the global training medical feature and the local training medical feature by using the fully connected layer, and performing image classification based on a fused feature obtained after the fusion to obtain a classification result; and respectively adjusting parameter values of the first network model, the second network model, and the fully connected layer based on an error between the classification result and the reference category.

In an embodiment, the computer program, when executed by the processor, causes the processor to perform the following steps:

respectively performing image processing on the medical image samples in image processing manners of different types to obtain a plurality of groups of medical image samples.

The computer program, when executed by the processor, causes the processor to further perform the following step:

extracting a training texture feature matrix based on the data of the ROI in the plurality of groups of medical image samples; and generating the training texture image based on the training texture feature matrix.

The computer program, when executed by the processor, further causes the processor to perform the following steps:

obtaining the error between the classification result and the reference category; back-propagating the error to neurons of the first network model, the second network model, and the fully connected layer to obtain a gradient of parameter values of the neurons; and updating the parameter values of the neurons based on the gradient.

The display screen of the computer device may be a liquid crystal display screen or an e-ink display screen. The input apparatus of the computer device may be a touch layer covering the display screen, or a button, a trackball, or a touchpad disposed on a housing of the computer device, or an external keyboard, touchpad, mouse, or the like.

A person skilled in the art may understand that the structure shown in FIG. 14 is only a block diagram of a partial structure related to the solution of this application, and does not limit the computer device to which the solution of this application is applied. Specifically, the computer device may include more or fewer components than those shown in the figure, or some components may be combined, or different component deployment may be used.

In an embodiment, the image classification apparatus provided in this application may be implemented in a form of a computer program, and the computer program may be run on the computer device shown in FIG. 14. A memory in the computer device may store program modules included in the image classification apparatus, for example, the image obtaining module 1202, the image generation module 1204, the first feature extraction module 1206, the second feature extraction module 1208, and the image classification module 1210 that are shown in FIG. 12. A computer program formed by the program modules causes the processor to perform the steps in the image classification method in the embodiments of this application described in this specification.

For example, the computer device shown in FIG. 14 may perform S202 by using the image obtaining module 1202 in the image classification apparatus shown in FIG. 12. The computer device may perform S204 by using the image generation module 1204. The computer device may perform S206 by using the first feature extraction module 1206. The computer device may perform S208 by using the second feature extraction module 1208. The computer device may perform S210 by using the image classification module 1210.

In an embodiment, a computer device is provided, including a processor and a memory, the memory storing a computer program, the computer program, when executed by the processor, causing the processor to perform the steps of the foregoing image classification method. The steps in the image classification method may be the steps in the image classification method in the foregoing embodiments.

In an embodiment, a non-transitory computer readable storage medium is provided, storing a computer program, the computer program, when executed by a processor, causing the processor to perform the steps of the foregoing image classification method. The steps in the image classification method may be the steps in the image classification method in the foregoing embodiments.

A person of ordinary skill in the art may understand that all or some of the processes of the methods in the foregoing embodiments may be implemented by a computer program instructing relevant hardware. The program may be stored in a non-volatile computer-readable storage medium. When the program runs, the processes of the foregoing methods in the embodiments are performed. Any reference to a memory, a storage, a database, or another medium used in the embodiments provided in this application may include a non-volatile and/or volatile memory. The non-volatile memory may include a read-only memory (ROM), a programmable ROM (PROM), an electrically programmable ROM (EPROM), an electrically erasable programmable ROM (EEPROM), a flash memory, or the like. The volatile memory may include a random access memory (RAM) or an external cache. As an illustration instead of a limitation, the RAM is available in various forms, such as a static RAM (SRAM), a dynamic RAM (DRAM), a synchronous DRAM (SDRAM), a double data rate SDRAM (DDRSDRAM), an enhanced SDRAM (ESDRAM), a synchronization link (Synchlink) DRAM (SLDRAM), a Rambus direct RAM (RDRAM), a direct Rambus dynamic RAM (DRDRAM), and a Rambus dynamic RAM (RDRAM).

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

The foregoing embodiments show only several implementations of this application and are described in detail, which, however, are not to be construed as a limitation to the patent scope of this application. For a person of ordinary skill in the art, several transformations and improvements can be made without departing from the idea of this application. These transformations and improvements belong to the protection scope of this application. Therefore, the protection scope of the patent of this application shall be subject to the appended claims.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs image classification and/or training. In practical application, the foregoing functions may be allocated to and completed by different functional modules according to requirements, that is, an inner structure of a device is divided into different functional modules to implement all or a part of the functions described above

What is claimed is:

1. An image classification method, applicable to a computer device, the method comprising:
obtaining a plurality of medical images;
generating a texture image based on image data of a region of interest (ROI) in the medical images;
extracting a local feature from the texture image using a first network model;
extracting a global feature from the medical images using a second network model;
fusing the extracted local feature and the extracted global feature to form a fused feature using a fully connected layer;
performing convolution calculation on the fused feature; and
performing image classification on the medical images based on a result obtained through the convolution calculation of the fused feature.

2. The method according to claim 1, further comprising obtaining the ROI in the medical images, the obtaining including:
obtaining medical image samples having segmentation labels;
inputting the medical image samples to an image segmentation network for segmentation to obtain a predicted region of interest; and
inputting the obtained medical images to a trained image segmentation network for image segmentation when the predicted region of interest matches the segmentation labels, to obtain the region of interest of the medical images.

3. The method according to claim 1, further comprising obtaining the ROI in the medical images, the obtaining including:
  receiving an input that defines the ROI in the medical images and defining the ROI in accordance with the input; or
  obtaining pixel values of the medical images, and obtaining, when pixel values meet a target condition, a region corresponding to the pixel values meeting the target condition as the ROI.

4. The method according to claim 1, wherein the generating the texture image further comprises:
  obtaining a texture feature matrix based on the image data of the ROI;
  obtaining a target size based on a size of the texture feature matrix; and
  performing image rendering based on the texture feature matrix to obtain the texture image having the target size.

5. The method according to claim 4, wherein obtaining the texture feature matrix further comprises:
  selecting a pixel value interval;
  obtaining pixel combinations of pixel values in the pixel value interval;
  calculating frequencies at which pixels corresponding to the pixel values in the pixel combinations appear in the ROI to obtain frequency sets; and
  converting frequencies in the frequency sets into probabilities to obtain the texture feature matrix.

6. The method according to claim 5, wherein calculating the frequencies further comprises:
  obtaining a target distance and a calculation direction, there being a plurality of calculation directions;
  obtaining, from the region of interest, a pixel that matches the target distance;
  calculating, based on each of the calculation directions, a number of pixels that correspond to pixel values in each of the pixel combinations and that match the pixel meeting the target distance; and
  obtaining a matching quantity as the frequencies to obtain the plurality of frequency sets corresponding to a quantity of the calculation directions.

7. The method according to claim 6, wherein converting the frequencies in the frequency sets into probabilities to obtain the texture feature matrix comprises:
  obtaining a quantity of channels of the medical images;
  converting the frequencies in the plurality of frequency sets into the probabilities, and calculating a mean of probabilities at corresponding positions in the plurality of frequency sets after the conversion;
  obtaining, based on the mean of the probabilities, mean probability sets with a quantity consistent with the quantity of channels; and
  obtaining the mean probability sets as the texture feature matrix.

8. The method according to claim 1, further comprising:
  obtaining medical image samples of different image types and a corresponding reference category;
  generating a training texture image based on data of a region of interest in the medical image samples;
  extracting a feature of the training texture image using the first network model, to obtain a local training medical feature;
  extracting features of the medical image samples using the second network model, to obtain a global training medical feature;
  fusing the global training medical feature and the local training medical feature by using the fully connected layer;
  performing image classification based on a fused feature obtained after the fusion to obtain a classification result; and
  respectively adjusting parameter values of the first network model, the second network model, and the fully connected layer based on an error between the classification result and the reference category.

9. The method according to claim 8, further comprising:
  performing image processing on the medical image samples different the different image types to obtain a plurality of groups of medical image samples; and
  generating the training texture image further comprises:
    extracting a training texture feature matrix based on the data of the region of interest in the plurality of groups of medical image samples; and
    generating the training texture image based on the training texture feature matrix.

10. The method according to claim 8, wherein the respectively adjusting parameter values of the first network model, the second network model, and the fully connected layer based on an error between the classification result and the reference category further comprises:
  determining the error between the classification result and the reference category;
  back-propagating the error to neurons of the first network model, the second network model, and the fully connected layer to obtain a gradient of parameter values of the neurons; and
  updating the parameter values of the neurons based on the gradient.

11. A computer device, comprising:
  one or more processors; and
  memory storing one or more programs, that, when executed by the one or more processors, cause the one or more processors to perform operations comprising:
    obtaining a plurality of medical images;
    generating a texture image based on image data of a region of interest (ROI) in the medical images;
    extracting a local feature from the texture image using a first network model;
    extracting a global feature from the medical images using a second network model;
    fusing the extracted local feature and the extracted global feature to form a fused feature using a fully connected layer;
    Performing convolution calculation on the fused feature; and
    performing image classification on the medical images based on a result obtained through the convolution calculation of the fused feature.

12. The computer device according to claim 11, the operations further comprising obtaining the ROI in the medical images, the obtaining including:
  obtaining medical image samples having segmentation labels;
  inputting the medical image samples to an image segmentation network for segmentation to obtain a predicted region of interest; and
  inputting the obtained medical images to a trained image segmentation network for image segmentation when the predicted region of interest matches the segmentation labels, to obtain the region of interest of the medical images.

13. The computer device according to claim 11, the operations further comprising obtaining the ROI in the medical images, the obtaining including:
  receiving an input that defines the ROI in the medical images and defining the ROI in accordance with the input; or
  obtaining pixel values of the medical images, and obtaining, when pixel values meet a target condition, a region corresponding to the pixel values meeting the target condition as the ROI.

14. The computer device according to claim 11, wherein generating the texture image further comprises:
  obtaining a texture feature matrix based on the image data of the ROI;
  obtaining a target size based on a size of the texture feature matrix; and
  performing image rendering based on the texture feature matrix to obtain the texture image having the target size.

15. The computer device according to claim 14, wherein obtaining the texture feature matrix further comprises:
  selecting a pixel value interval;
  obtaining pixel combinations of pixel values in the pixel value interval;
  calculating frequencies at which pixels corresponding to the pixel values in the pixel combinations appear in the ROI to obtain frequency sets;
  converting frequencies in the frequency sets into probabilities to obtain the texture feature matrix.

16. The computer device according to claim 15, wherein calculating the frequencies further comprises:
  obtaining a target distance and a calculation direction, there being a plurality of calculation directions;
  obtaining, from the region of interest, a pixel that matches the target distance;
  calculating, based on each of the calculation directions, a number of pixels that correspond to pixel values in each of the pixel combinations and that match the pixel meeting the target distance; and
  obtaining a matching quantity as the frequencies to obtain the plurality of frequency sets corresponding to a quantity of the calculation directions.

17. A non-transitory computer readable storage medium storing instructions that, when executed by one or more processors of a computer device, cause the one or more processors to perform operations comprising:
  obtaining a plurality of medical images;
  generating a texture image based on image data of a region of interest (ROI) in the medical images;
  extracting a local feature from the texture image using a first network model;
  extracting a global feature from the medical images using a second network model;
  fusing the extracted local feature and the extracted global feature to form a fused feature using a fully connected layer;
  performing convolution calculation on the fused feature; and
  performing image classification on the medical images based on a result obtained through the convolution calculation of the fused feature.

18. The non-transitory computer readable storage medium according to claim 17, the operations further comprising obtaining the ROI in the medical images, the obtaining including:
  obtaining medical image samples having segmentation labels;
  inputting the medical image samples to an image segmentation network for segmentation to obtain a predicted region of interest; and
  inputting the obtained medical images to a trained image segmentation network for image segmentation when the predicted region of interest matches the segmentation labels, to obtain the region of interest of the medical images.

19. The non-transitory computer readable storage medium according to claim 17, the operations further comprising obtaining the ROI in the medical images, the obtaining including:
  receiving an input that defines the ROI in the medical images and defining the ROI in accordance with the input; or
  obtaining pixel values of the medical images, and obtaining, when pixel values meet a target condition, a region corresponding to the pixel values meeting the target condition as the ROI.

* * * * *